(12) United States Patent
Kreifels et al.

(10) Patent No.: US 9,932,632 B2
(45) Date of Patent: Apr. 3, 2018

(54) REAL-TIME OPTICAL SYSTEM FOR POLYMERASE CHAIN REACTION

(71) Applicant: Streck, Inc., LaVista, NE (US)

(72) Inventors: Matthew R. Kreifels, Omaha, NE (US); Scott E. Whitney, Lincoln, NE (US); Joel R. TerMaat, Lincoln, NE (US)

(73) Assignee: Streck, Inc., LaVista, NE (US)

( * ) Notice: Subject to any disclaimer, the term of this patent is extended or adjusted under 35 U.S.C. 154(b) by 690 days.

(21) Appl. No.: 13/833,349

(22) Filed: Mar. 15, 2013

(65) Prior Publication Data

US 2014/0045250 A1    Feb. 13, 2014

Related U.S. Application Data

(60) Provisional application No. 61/681,879, filed on Aug. 10, 2012, provisional application No. 61/752,494, filed on Jan. 15, 2013.

(51) Int. Cl.
*G01N 21/00* (2006.01)
*C12Q 1/68* (2018.01)
*G01N 21/64* (2006.01)

(52) U.S. Cl.
CPC ........... *C12Q 1/686* (2013.01); *G01N 21/645* (2013.01); *G01N 21/6452* (2013.01); *G01N 2021/6484* (2013.01); *G01N 2201/0627* (2013.01); *G01N 2201/0826* (2013.01); *G01N 2201/0833* (2013.01)

(58) Field of Classification Search
CPC ............ C12C 1/686; G01N 2021/6484; G01N 21/645; G01N 21/6452; G01N 2201/0627; G01N 2201/0826; G01N 2201/0833; C12Q 1/686
USPC ........................................... 435/283.1–309.4
See application file for complete search history.

(56) References Cited

U.S. PATENT DOCUMENTS

| 3,722,502 | A | 3/1973 | Besuner et al. |
| 3,911,918 | A | 10/1975 | Turner |
| D255,526 | S | 6/1980 | Dempster |
| D256,053 | S | 7/1980 | Steigerwald |
| 4,528,187 | A | 7/1985 | Truglio |
| 4,674,640 | A | 6/1987 | Asa et al. |
| 4,683,202 | A | 7/1987 | Mullis |
| 4,900,321 | A | 2/1990 | Kaufman et al. |
| 4,902,624 | A | 2/1990 | Columbus et al. |

(Continued)

FOREIGN PATENT DOCUMENTS

| DE | 4 022 792 A1 | 2/1992 |
| EP | 0 350 672 A2 | 1/1990 |

(Continued)

OTHER PUBLICATIONS

PCT International Preliminary Report on Patentability dated Oct. 22, 2014 (Appln. No. PCT/US2013/031910).

(Continued)

*Primary Examiner* — Jonathan M Hurst
(74) *Attorney, Agent, or Firm* — The Dobrusin Law Firm, P.C.

(57) ABSTRACT

An improved device and system for facilitating polymerase chain reaction including a light source, detector, waveguide, and filters that occupy minimal space and facilitate reduced sample read time and rapid reading of multiple light wavelengths.

20 Claims, 16 Drawing Sheets

(56) References Cited

U.S. PATENT DOCUMENTS

| | | | |
|---|---|---|---|
| D313,098 S | 12/1990 | Boyd et al. | |
| 5,084,041 A | 1/1992 | Oxley et al. | |
| 5,098,661 A * | 3/1992 | Froehlich | B01L 3/545 356/246 |
| D330,428 S | 10/1992 | Lewis et al. | |
| D337,261 S | 7/1993 | Sherman | |
| 5,225,165 A | 7/1993 | Perlman | |
| 5,229,327 A | 7/1993 | Farnworth | |
| 5,270,011 A | 12/1993 | Altherr | |
| 5,304,487 A | 4/1994 | Wilding et al. | |
| 5,333,675 A | 8/1994 | Mullis et al. | |
| 5,337,139 A * | 8/1994 | Shirasawa | G01N 21/253 250/461.1 |
| 5,353,186 A | 10/1994 | Ruoss et al. | |
| 5,423,792 A | 6/1995 | Oxley | |
| 5,455,175 A | 10/1995 | Witterwer et al. | |
| 5,475,610 A | 12/1995 | Atwood et al. | |
| 5,508,197 A | 4/1996 | Hansen et al. | |
| 5,525,300 A | 6/1996 | Danssaert et al. | |
| 5,540,892 A | 7/1996 | Kidd et al. | |
| 5,571,479 A | 11/1996 | Koch | |
| 5,576,218 A | 11/1996 | Zurek et al. | |
| 5,598,349 A | 1/1997 | Elliason et al. | |
| 5,604,101 A | 2/1997 | Hanley et al. | |
| 5,656,493 A | 8/1997 | Mullis et al. | |
| 5,674,742 A | 10/1997 | Northrup et al. | |
| 5,681,741 A | 10/1997 | Atwood et al. | |
| 5,683,659 A | 11/1997 | Hovatter | |
| 5,721,136 A | 2/1998 | Finney et al. | |
| 5,795,547 A | 8/1998 | Moser et al. | |
| 5,832,543 A | 11/1998 | Bosserman | |
| 5,856,174 A | 1/1999 | Lipshutz et al. | |
| 5,863,791 A | 1/1999 | Baldszun et al. | |
| 5,928,880 A | 7/1999 | Wilding | |
| 5,928,907 A | 7/1999 | Woudenberg et al. | |
| 5,935,858 A | 8/1999 | Herst | |
| 5,958,349 A | 9/1999 | Petersen et al. | |
| 5,972,716 A | 10/1999 | Ragusa et al. | |
| 6,015,534 A | 1/2000 | Atwood | |
| D425,625 S | 5/2000 | Niermann | |
| 6,140,613 A | 10/2000 | Isuno | |
| 6,144,448 A | 11/2000 | Mitoma | |
| 6,159,727 A | 12/2000 | Bochkariov | |
| 6,210,382 B1 | 4/2001 | Hogg | |
| 6,210,958 B1 | 4/2001 | Brust et al. | |
| 6,303,343 B1 | 10/2001 | Kopf-Sill | |
| 6,312,886 B1 | 11/2001 | Lee et al. | |
| 6,372,486 B1 | 4/2002 | Fripp | |
| 6,372,895 B1 * | 4/2002 | Bentsen | C07H 17/075 530/300 |
| 6,374,684 B1 | 4/2002 | Dority | |
| 6,392,241 B1 | 5/2002 | Rushbrooke | |
| 6,472,186 B1 | 10/2002 | Quintanar et al. | |
| 6,503,750 B1 | 1/2003 | Benett et al. | |
| 6,556,940 B1 | 4/2003 | Tretiakov et al. | |
| 6,558,947 B1 | 5/2003 | Lund et al. | |
| 6,645,191 B1 | 11/2003 | Knerr et al. | |
| 6,657,169 B2 | 12/2003 | Brown et al. | |
| 6,734,401 B2 | 5/2004 | Bedingham et al. | |
| 6,780,617 B2 | 8/2004 | Chen | |
| 6,783,025 B2 | 8/2004 | Lohn | |
| 6,783,736 B1 | 8/2004 | Taylor et al. | |
| 6,787,338 B2 | 9/2004 | Wittwer et al. | |
| 6,814,934 B1 | 11/2004 | Higuchi | |
| 6,818,185 B1 | 11/2004 | Petersen et al. | |
| 6,875,602 B2 | 4/2005 | Gutierrez | |
| 6,881,541 B2 | 4/2005 | Petersen et al. | |
| 6,887,693 B2 | 5/2005 | McMillan et al. | |
| 6,889,468 B2 | 5/2005 | Bedingham et al. | |
| 6,964,862 B2 | 11/2005 | Chen | |
| 6,987,253 B2 | 1/2006 | Bedingham et al. | |
| 7,051,536 B1 | 5/2006 | Cohen et al. | |
| 7,081,600 B2 | 7/2006 | Brown et al. | |
| 7,138,254 B2 | 11/2006 | Jovanovich et al. | |
| 7,164,077 B2 | 1/2007 | Venkatasubramanian et al. | |
| 7,164,107 B2 | 1/2007 | Bedingham et al. | |
| 7,189,252 B2 | 3/2007 | Krueger et al. | |
| 7,238,321 B2 | 7/2007 | Wittwer et al. | |
| 7,255,833 B2 | 8/2007 | Chang et al. | |
| 7,295,316 B2 | 11/2007 | Boege et al. | |
| 7,422,905 B2 | 9/2008 | Clague et al. | |
| 7,435,933 B2 | 10/2008 | Bedingham et al. | |
| 7,439,069 B2 | 10/2008 | Nippoldt et al. | |
| 7,442,542 B2 | 10/2008 | Miao et al. | |
| 7,462,323 B1 | 12/2008 | Chang et al. | |
| 7,482,116 B2 | 1/2009 | Birnboim | |
| 7,490,976 B2 | 2/2009 | Bucher | |
| 7,507,575 B2 | 3/2009 | Bedingham et al. | |
| 7,544,506 B2 | 6/2009 | Breidford et al. | |
| 7,578,976 B1 | 8/2009 | Northrup et al. | |
| 7,648,095 B2 | 1/2010 | Jagle | |
| 7,749,452 B2 | 7/2010 | Brem et al. | |
| D621,520 S | 8/2010 | Talmer et al. | |
| D621,951 S | 8/2010 | Bucholtz et al. | |
| D640,795 S | 6/2011 | Jackson et al. | |
| 8,003,370 B2 | 8/2011 | Maltezos et al. | |
| 8,008,046 B2 | 8/2011 | Maltezos et al. | |
| 8,137,616 B2 | 3/2012 | Sagner et al. | |
| 2002/0086417 A1 | 7/2002 | Chen | |
| 2004/0122559 A1 | 6/2004 | Young | |
| 2004/0214315 A1 | 10/2004 | Saluz et al. | |
| 2005/0282270 A1 | 12/2005 | Shin et al. | |
| 2006/0088931 A1 | 4/2006 | Ririe | |
| 2006/0101830 A1 | 5/2006 | Cohen et al. | |
| 2006/0160243 A1 | 7/2006 | Tang et al. | |
| 2006/0228264 A1 | 10/2006 | Garvin et al. | |
| 2007/0051739 A1 | 3/2007 | Giraud | |
| 2007/0065074 A1 * | 3/2007 | Hillendahl | G01N 21/6452 385/33 |
| 2007/0111206 A1 | 5/2007 | Tyagi et al. | |
| 2007/0128080 A1 | 6/2007 | Lohn | |
| 2007/0140919 A1 | 6/2007 | Clarkson et al. | |
| 2007/0230182 A1 * | 10/2007 | Tai | F21V 17/06 362/294 |
| 2008/0003649 A1 | 1/2008 | Maltezos et al. | |
| 2008/0038813 A1 | 2/2008 | Chen | |
| 2008/0061429 A1 | 3/2008 | Cohen et al. | |
| 2008/0193912 A1 | 8/2008 | Fong et al. | |
| 2008/0219889 A1 | 9/2008 | Schaefer et al. | |
| 2008/0248534 A1 | 10/2008 | Lim et al. | |
| 2009/0011417 A1 | 1/2009 | Maltezos et al. | |
| 2009/0023603 A1 | 1/2009 | Selden et al. | |
| 2009/0061450 A1 | 3/2009 | Hunter | |
| 2009/0079975 A1 * | 3/2009 | Green | G01N 21/645 356/244 |
| 2009/0120104 A1 | 5/2009 | Federer | |
| 2009/0136385 A1 | 5/2009 | Handique et al. | |
| 2009/0155838 A1 | 6/2009 | Hale | |
| 2009/0162866 A1 | 6/2009 | Birnboim et al. | |
| 2009/0275113 A1 | 11/2009 | Maltetos et al. | |
| 2010/0288059 A1 | 5/2010 | Viljoen et al. | |
| 2010/0137166 A1 * | 6/2010 | Kain | C12Q 1/686 506/39 |
| 2010/0285571 A1 | 11/2010 | Coursey et al. | |
| 2010/0291536 A1 | 11/2010 | Viljoen et al. | |
| 2011/0039305 A1 * | 2/2011 | Termaat | B01L 7/52 435/91.2 |
| 2011/0311978 A1 * | 12/2011 | Makarewicz, Jr. | B01F 3/0807 435/6.12 |
| 2012/0014835 A1 * | 1/2012 | Howell et al. | 422/52 |
| 2014/0176940 A1 * | 6/2014 | Fishbine | G01J 3/0218 356/301 |
| 2015/0111287 A1 * | 4/2015 | Rawle | B01L 7/52 435/287.2 |

FOREIGN PATENT DOCUMENTS

| | | |
|---|---|---|
| EP | 1757367 | 2/2007 |
| EP | 1962084 | 8/2008 |
| EP | 1962084 A1 | 8/2008 |
| EP | 2193845 | 6/2010 |
| WO | 98/43740 A2 | 10/1998 |
| WO | 01/15680 A1 | 3/2001 |

(56) References Cited

FOREIGN PATENT DOCUMENTS

| WO | 2004/052527 A1 | 6/2004 |
|---|---|---|
| WO | 2005/113741 A1 | 12/2005 |
| WO | 2006/024879 | 3/2006 |
| WO | 2009/009124 | 1/2009 |
| WO | 2009/009124 A1 | 1/2009 |
| WO | 2009/105499 A1 | 8/2009 |
| WO | 2010/079338 | 7/2010 |
| WO | 2010/079338 A2 | 7/2010 |
| WO | 2010/091400 | 8/2010 |
| WO | 2010/091400 A2 | 8/2010 |
| WO | 2011082415 | 7/2011 |
| WO | 2011086497 | 7/2011 |
| WO | 2011/153244 | 12/2011 |

OTHER PUBLICATIONS

International Search Report and Written Opinion dated Jul. 10, 2009, for Corresponding PCT Application No. US2009/34446 A1 filed Feb. 19, 2009.

Northrup et al., A Miniature Integrated Nucleic Acid Analysis System, Automation Technologies for Genome characterization, 1997, 189-204.

Boshofe-Mostert et al., Crack propagation in catalytic pellets due to thermal stresses, Aiche J. Aug. 1996, 2288-2294, 42.

Chaisson et al., Tuberculosis in Africa—Combating an HIV driven crisis. N. Engl. J. Med., Mar. 13, 2008, 1089-1092, 358(11).

Davies et al., The diagnosis and misdiagnosis of tuberculosis, Int. J. Tubere, Lunc. Dis., Nov. 2008, 1226-1234, 12(11).

Davis et al., The rheological properties of sputum, Biorheology, Apr. 1969, 11-21, 6(1).

Dziadek et al., Specificity of insertion sequence-based PCR assays for *Mycobacterium tuberculosis* complex, Int. J. Tuberc. Lung. Dis., Jan. 2001, 569-574, 5(6).

El-Hajj et al., Detection of rifampin resistance in *Mycobacterium tuberculosis* in a single tube with molecular beacons, J. Clin. Microbiol., Nov. 2001, 4131-4137, 39(11).

Flores et al., In-house nucleic acid amplification tests for the detection of *Mycobacterium tuberculosis* in sputum specimens: meta-analysis and meta-regression, BMC Microbiol., Oct. 2005, 55, 5.

Friedman et al., Capillary Tube Resistive Thermal Cycling, Anal. Chem., Jul. 15, 1998, 2997-3002, 70(14).

Global Health Diagnostics Forum, The right tools can save lives, Nature, Dec. 7, 2006, 681, 444.

Greco et al., Current evidence on diagnostic accuracy of commercially based nucleic acid amplification tests for the diagnosis of pulmonary tuberculosis, Thorax, Sep. 2006, 783-790, 61(9).

Griep et al., Kinetics of the DNA polymerase *Pyrococcus kodakaraensis*. Chemical Engineering Science, 2006, 3885-3892 61.

Keeler et al., Reducing the global burden of tuberculosis: The contribution of improved diagnostics, Nature, Nov. 23, 2006, 49-57, 444 Supp. 1.

Marras et al., Genotyping SNPs with molecular beacons, Methods Mol. Biol. 2003, 111-128, 212.

McEvoy et al., The role of IS6110 in the evolution of *Mycobacterium tuberculosis*, Tuberculosis (Edinb)., Sep. 2007, 393-404, 87(5).

Menzies et al., Risk of tuberculosis infection and disease associated with work in health care settings, Int. J. Tuberc. Lung Dis Jun. 2007, 593-605, 11(6).

Menzies et al., Tuberculosis among health care workers, N. Engl. J. Med., Jan. 12, 1995, 92-98, 332(2).

Musser, Antimicrobial agent resistance in mycobacteria: genetic insights, Clin. Microbiol. Rev., Oct. 1995, 496-514, 8(4).

Muthupillai et al., Magnetic resonance elastography by direct visualization of propagating acoustic strain waves, Science, Sep. 29, 1995, 1854-1857, 269.

Negi et al., Diagnostic potential of IS6110, 38kDa, 65kDa and 85B sequence-based polymerase chain reaction in the diagnosis of *Mycobacterium tuberculosis* in clinical samples, Indian. J. Med. Microbiol. Jan. 2007, 43-49, 25(1).

Nielsen et al., Elastic contributions dominate the viscoelastic properties of sputum from cystic fibrosis patient, Biophys. Chem., Dec. 20, 2004, 193-200, 112.

Othman et al., Microscopic magnetic resonance elastography (muMRE), Magnetic Resonance in Medicine, Sep. 2005, 605-615, 54.

Perkins et al., Progress towards improved tuberculosis diagnostics for developing countries, Lancet, Mar. 18, 2006, 942-943, 367.

Ramaswamy et al., Molecular genetic basis of antimicrobial agent resistance in *Mycobacterium tuberculosis*: 1998 update, Tuber. Lung Dis., 1998. 3-29, 79.

Riska et al., Molecular determinants of drug resistance in tuberculosis, Int. J. Tuberc. Lung Dis., Feb. 2000, S4-10. 4(2 Suppl 1).

Sarmiento et al., Assessment by meta-analysis of PCR for diagnosis of smear-negative pulmonary tuberculosis, J. Clin. Microbiol., Jul. 2003, 3233-3240, 41(7).

Shah et al., Extensively Drug-Resistant Tuberculosis in the United States 1993-2007, JAMA, Nov. 12, 2008, 2153-2160, 300(18).

Singh et al., Comparative evaluation of FASTPlaque assay with PCR and other conventional in vitro diagnostic methods for the early detection of pulmonary tuberculosis, J. Clin. Lab. Anal., 2008, 367-374, 22(5).

Somoskovi et al., The molecular basis of resistance to isoniazid, rifampin, and pyrazinamide in *Mycobacterium tuberculosis*, Respir. Res., 2001, 164-168, 2(3).

Storla et al., A systematic review of delay in the diagnosis and treatment of tuberculosis, BMC Public Health, Jan. 14, 2008, 15, 8.

Sun et al., Comparison of gyrA gene mutations between laboratory-selected ofloxacin-resistant *Mycobacterium tuberculosis* strains and clinical isolates, Int. J. Antimicrob, Agents., Feb. 2008, 115-112, 31(2).

Telenti, Genetics and pulmonary medicine. 5. Genetics of drug resistant tuberculosis, Thorax, Sep. 2008, 793-797, 53.

Thierry et al., Characterization of a *Mycobacterium tuberculosis*insertion sequence, IS6110, and its application in diagnosis, J. Clin. Microbiol., Dec. 1990, 2668-2673, 28(12).

Valente et al., A kinetic study of in virtu lysis of *Mycobacterium smegmatis*, Chemical Engineering Science, 2009, 1944-1952, 64.

Van Soolingen et al., Comparison of various repetitive DNA elements as genetic markers for strain differentiation and epidemiology of *Mycobacterium tuberculosis*, J. Clin. Microbiol., Aug. 1993, 1987-1995, 31.

Viljoen et al., A macroscopic kinetic model for DNA polymerase elongation and the high-fidelity nucleotide selection, Computational Biology and Chemistry, Apr. 2005, 101-110, 29.

Wang et al., Fluoroquinolone resistance in *Mycobacterium tuberculosis* isolates: associated genetic mutations and relationship to antimicrobial exposure, J. Antimicrob. Chemother., May 2007, 860-865.

Wittwer et al., Minimizing the Time Required for DNA Amplification by Efficient Heat Transfer to Small Samples, Anal. Biochem., May 1, 1990, 328-331, 186(2).

World Health Organization, Global tuberculosis control—epidemiology, strategy, financing, WHO Report 2009, WHO/HTM/TB/2009.411.

Copending U.S. Appl. No. 29/400,931.

Copending U.S. Appl. No. 13/452,419.

Analytical Biochemistry 186, 328-331 (1990) "Minimizing the Time Required for DNA Amplication by Efficient Heat Transfer to Small Samples".

PCT Written Opinion & Search Report for Application No. PCT/US2012/040201 dated Aug. 1, 2012.

Northrup, M. Allen, et al., "A miniature integrated nucleic acid analysis system", Automation Technologies for Genome Characterization, 1997, pp. 189-204.

Wittwer, Carl T. et al, "Minimizing the time required for DNA amplification by efficient heat transfer to small samples", Anal. Chem. 1998. 70, 2997-3002.

(56) References Cited

OTHER PUBLICATIONS

Friedman, Neal A., et al., "Capillary tube resistive thermal cycling", The 7$^{th}$ International Conference on Solid-State Sensors and Actuators, 924-926.
International Search Report & Written Opinion dated Aug. 16, 2012; Application No. PCT/US2012/034506.
International Search Report & Written Opinion dated Jun. 20, 2013; Application No. PCT/US2013/031910.

* cited by examiner

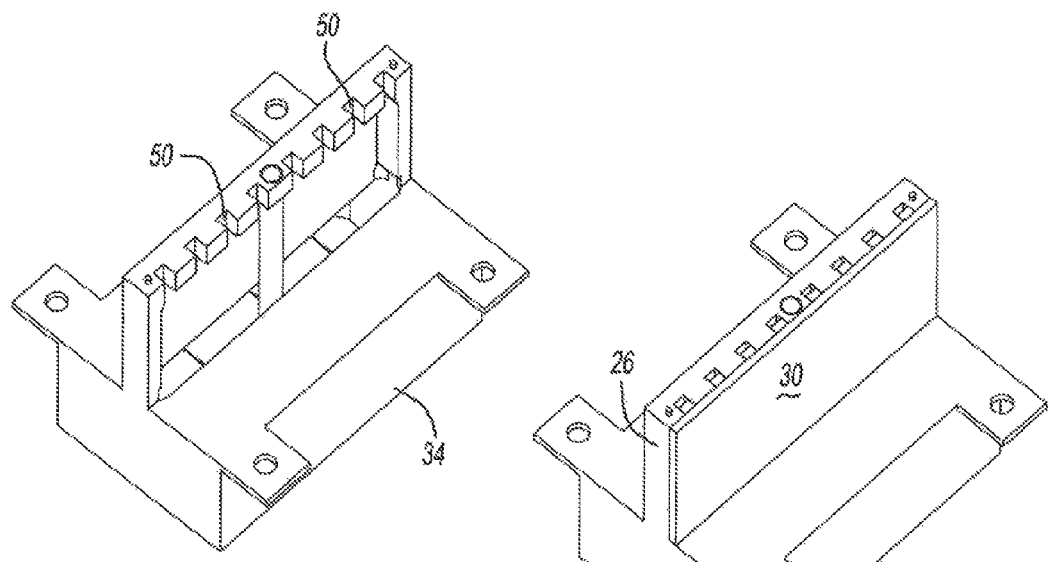
Fig-4A
Fig-4B
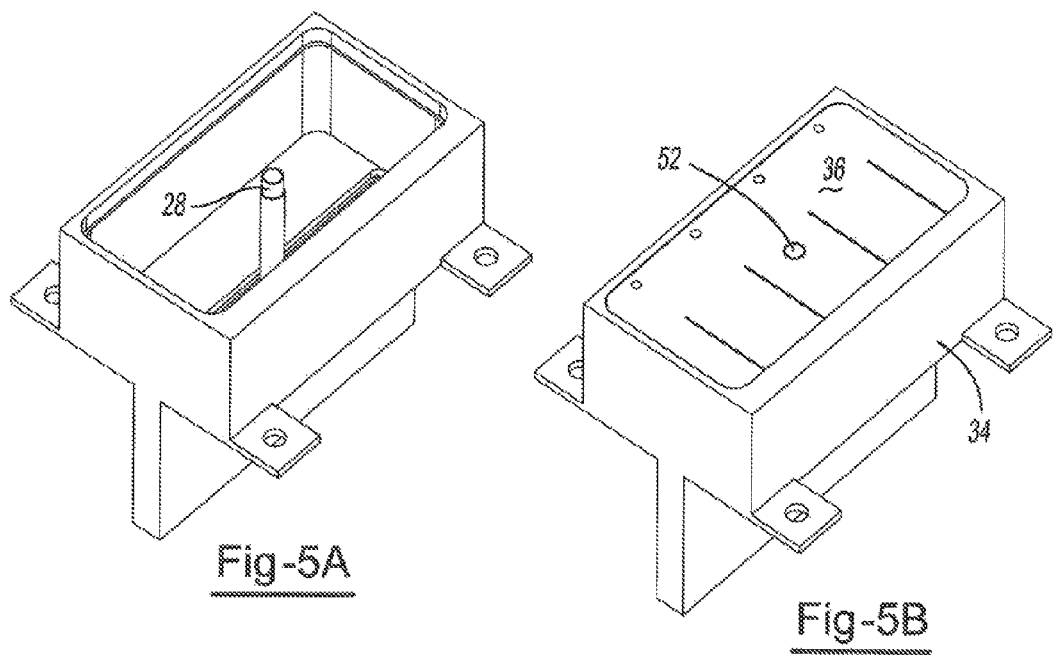
Fig-5A
Fig-5B

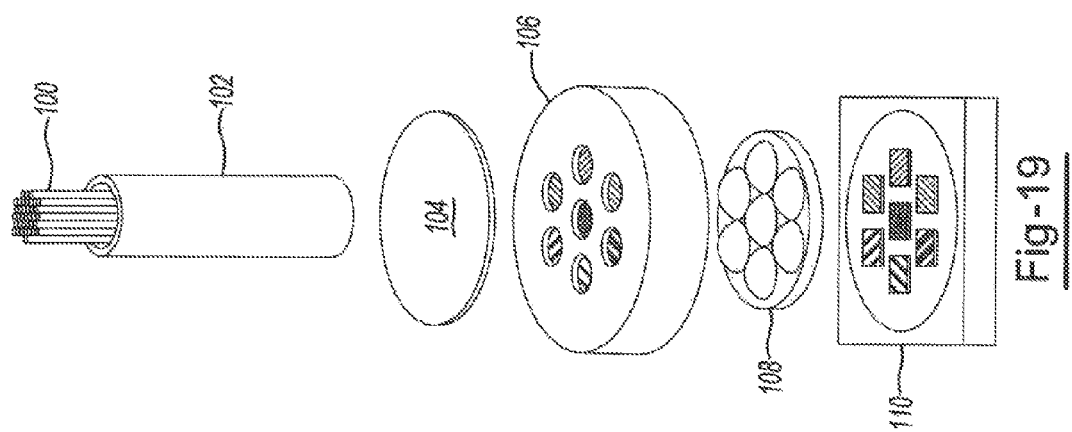
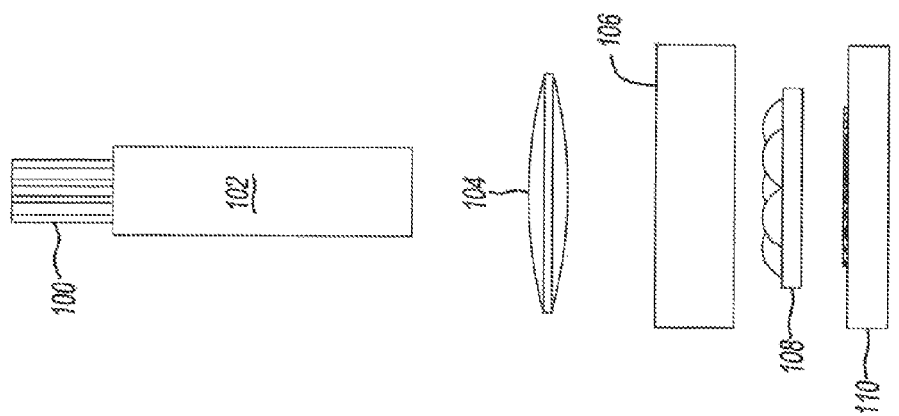

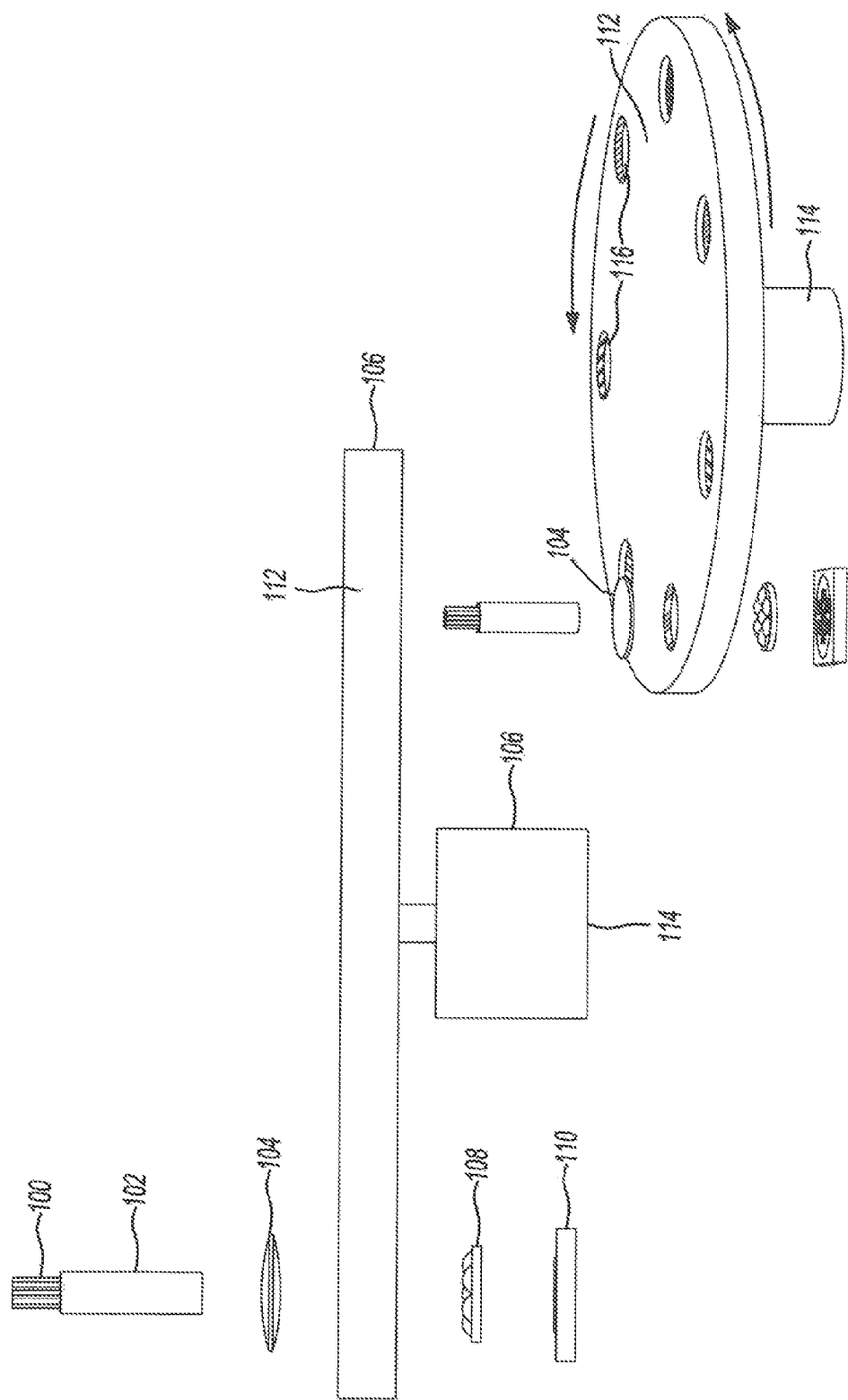

REAL-TIME OPTICAL SYSTEM FOR POLYMERASE CHAIN REACTION

FIELD OF THE INVENTION

The present invention relates generally to devices and systems for facilitating polymerase chain reactions.

BACKGROUND OF THE INVENTION

A number of optical detection systems have been developed for use in qualitative and quantitative nucleic acid measurements. Many such systems involve the use of fluorescing agents (fluorescent probes, markers, labels, or dyes) in which the resulting signal intensities are generally proportional to the reaction products of polymerase chain reaction (PCR) amplification.

As an example, U.S. Pat. No. 5,928,907 describes a system for facilitating real-time fluorescence-based measurements of nucleic acid amplification products utilizing a lens co-axially disposed with a fiber optic cable for focusing a single color excitation beam into the volume of a sample. U.S. Pat. No. 6,144,448 describes a fluorescence detecting device including direct fiber optic connections between a single light source, container holder and single fluorescence detector.

U.S. Pat. No. 7,315,376 describes a sample holder provided together with an optical manifold having an excitation source, a photo receiver, or both, for each sample. U.S. Pat. No. 7,507,575 describes a data acquisition device and a detection device coupled to the data acquisition device. The detection device includes a plurality of removable optical modules and a rotating disk having a plurality of process chambers having a plurality of species that emit fluorescent light at different wavelengths. U.S. Pat. No. 8,137,616 describes a system for performing multi-color real time PCR, comprising a flexible real time PCR instrument and a specific composition or reaction mixture for performing multiplex PCR.

There remains a need for an improved system and device for facilitating polymerase chain reaction that allows for detection of stationary samples, reduced sample read time and optionally simultaneous reading of multiple light wavelengths, resulting in an increase in the speed with which amplification and quantification take place. There is a further need for instruments that include multiple light sources and detectors that occupy minimal space and require little or no ancillary instrumentation for facilitating light provision, fluorescence detection, or movement of samples to read different samples or fluorescent wavelengths. There is a need for instruments that do not rely on precise and/or complex alignments of reflective components such as mirrors, enclosures, beam splitters, dichrotic/dichroric filters, or microelectronic mirrors for light routing. There is also a need for instruments that facilitate PCR and detection without direct connection between a sample holder and fiber optic cable.

SUMMARY OF THE INVENTION

The present teachings meet one or more of the above needs by providing an instrument for performing polymerase chain reaction with real-time detection, including a light source, detector, waveguide, and filters that occupy minimal space and facilitate detection of stationary samples, reduced sample read time, and simultaneous reading of multiple light wavelengths.

The present teachings provide for a device comprising a polymerase chain reaction instrument that includes a sample holder configured to receive one or more sample tubes that each have at least one portion that is generally optically transparent, and that receives a biological sample having a nucleic acid to be amplified and at least one fluorescing agent that interacts with the nucleic acid during amplification and that emits light upon excitation by light of a known wavelength. The instrument may further include at least one light emitting diode device (device being an integrated assembly of light emitting diodes or a compact group of light emitting diodes) that is carried on at least one support substrate, is in electrical communication with a power source, and is adapted to emit light at a plurality of different wavelengths, optionally through a lens. At least one photodiode detector device (the device being an integrated assembly of photodiodes (e.g. photodiode array), an individual photodiode or compact group of photodiodes) may also be included such that the detector is adapted to issue signals based upon intensity of light it receives. The instrument may also include a light transmission assembly that includes at least one multi-branched waveguide and at least one manifold (e.g., a fiber optics block) that is configured to support the waveguide between the sample holder and both the at least one light emitting diode device and the at least one photodiode detector device. The waveguide may include a first fork portion and a second fork portion. The waveguide may include at least one excitation fork portion and at least one emission fork portion. The first fork portion (e.g., at least one excitation fork portion) may extend between the sample holder and the light emitting diode device for transmitting light emitted from the light emitting diode device to the sample contained in the sample holder to excite the fluorescing agent. The second fork portion (e.g., at least one emission fork portion) may extend between the sample holder and the photodiode detector device for transmitting light emitted by the fluorescing agent upon its excitation and having a first end that is proximate the sample holder and a second end that is proximate the photodiode detector device. The instrument may include at least one single-band or multi-band bandpass filter such that the light emitted from the at least one light emitting diode device is filtered into at least one distinct wavelength band. The instrument may also include a linear variable bandpass filter, a series of bandpass filters, or a multi-band bandpass filter disposed between the second end of the second fork portion and the photodiode detector device and is adapted to filter the light emitted by the fluorescing agent so that the wavelengths of light received across the photodiode detector device are known.

The present teachings further provide for an instrument for performing polymerase chain reaction with real-time detection comprising a polymerase chain reaction instrument that includes a sample holder configured to receive one or more sample tubes that each have at least one portion that is generally optically transparent, and that receives a biological sample having a nucleic acid to be amplified and at least one fluorescing agent that interacts with the nucleic acid during amplification and that emits light upon excitation by light of a known wavelength, in which the signal is generally proportional to the amount of nucleic acid amplified. The instrument may further include a light emitting diode device that is carried on at least one support substrate, is in electrical communication with a power source, and is adapted to emit light at a plurality of different wavelengths, optionally through a common lens. At least one heat sink may be included, the heat sink being carried on the support substrate for dissipating heat from the at least one light emitting diode device. At least one photodiode detector device may also be included which is adapted to issue signals that are generally proportionally based upon intensity of light it receives. The instrument may also include a light transmission assembly that includes at least one multi-branched waveguide and at least one manifold that is configured to support the waveguide between the sample holder and both the at least one light emitting diode device and the at least one photodiode detector device. The waveguide may include a first fork portion and a second fork portion. The waveguide may include at least one excitation fork portion (e.g., the first fork portion) and at least one emission fork portion (e.g., the second fork portion). The first fork portion may extend between the sample holder and the light emitting diode device for transmitting light emitted from the light emitting diode device to the sample contained in the sample holder to excite the fluorescing agent. The second fork portion may extend between the sample holder and the photodiode detector device for transmitting light emitted by the fluorescing agent upon its excitation and having a first end that is proximate the sample holder and a second end that is proximate the photodiode detector device. The instrument may also include a linear variable band pass filter, a series of bandpass filters, or a multi-band bandpass filter disposed between the second end of the second fork portion and the photodiode detector device and adapted to filter the light emitted by the fluorescing agent so that the wavelengths of light received across the photodiode detector device are known.

The present teachings also provide for an instrument for performing polymerase chain reaction with real-time detection comprising a polymerase chain reaction instrument that includes a sample holder configured to receive one or more sample tubes that each have at least one portion that is generally optically transparent, and that receives a biological sample having a nucleic acid to be amplified and at least one fluorescing agent that interacts with the nucleic acid during amplification and that emits light upon excitation by light of a known wavelength. The instrument may further include a light emitting diode device that is carried on at least one support substrate, is in electrical communication with a power source, and includes at least four (preferably at least five) light emitting diodes each adapted to emit light at a different wavelength relative to each other, optionally through a single common lens or optic fiber fork. At least one heat sink may be carried on the support substrate for dissipating heat from the at least one light emitting diode device and at least one photodiode detector device may be included and adapted to issue signals that, are generally proportionally based upon intensity of light it receives and optionally including a plurality of discrete pixels or photodiodes. A light transmission assembly may also be included that is positioned below the sample holder and that includes at least one multi-branched waveguide and at least one manifold that includes a cavity and is configured with flanges to mount to within the polymerase chain reaction instrument to support the waveguide between the sample holder and both the at least one light emitting diode device and the at least one photodiode detector device. The waveguide may include a first and second fork portion. The waveguide may include at least one excitation fork portion and at least one emission fork portion. The first fork portion may extend through the cavity and between the sample holder and the light emitting diode device for transmitting light emitted from the light emitting diode device to the sample contained in the sample holder to excite the fluorescing agent. The second fork portion may extend through the cavity and between the sample holder and the photodiode array for transmitting light emitted by the fluorescing agent upon its excitation and having a first end that is proximate the sample holder and a second end that is proximate the photodiode detector device. The waveguide may also include a cover portion for the cavity of the manifold that includes a port that is aligned with the light emitting diode device and an opening for aligning the second end of the second fork portion with the photodiode detector device. The instrument may also include a linear variable bandpass filter that is disposed between the second end of the second fork portion and the photodiode array, wherein the linear variable filter includes a bandpass filter coating that is intentionally wedged in one direction, so that the peak wavelength transmitted through the filter varies in a linear fashion in the direction of the wedge, and wherein the linear variable filter is generally optically aligned with predetermined discrete pixels of the photodiode array, so that the wavelengths of light received by the discrete pixels of the photodiode array are known upon detection of light by the array. The instrument may also include a series of bandpass filters that is disposed between the second end of the second fork portion and the photodiode array, wherein each bandpass filter of the series is generally optically aligned with predetermined discrete pixels or photodiodes of the photodiode detector device, so that the wavelengths of light received by the discrete pixels or photodiodes of the photodiode detector device are known upon detection of light by the array.

As will be seen, the instrument described herein offers a unique approach to providing a modular PCR device providing relatively high-speed PCR amplification and detection by virtue of the device's ability to provide reduced sample read time, and the ability to quickly detect light at multiple wavelengths. The instrument described herein may not rely upon reflective components which are expensive or difficult to align for the routing of light. The instrument described herein may not rely upon a direct connection from the sample holder and a fiber optic cable.

DESCRIPTION OF THE DRAWINGS

FIG. 4A is a perspective view of an illustrative fiber optics block.

FIG. 4B is a perspective view of the fiber optics block of FIG. 4A shown with an illustrative fiber optics cap.

FIG. 5A is a perspective view of the fiber optics block of FIG. 4A shown from beneath the block.

FIG. 5B is a perspective view of the fiber optics block of FIG. 5A shown with an illustrative bottom alignment cover.

FIG. 18 is an exploded side profile view of an illustrative fork portion in accordance with the present teachings.

FIG. 19 is an exploded perspective view of the fork portion of FIG. 18.

FIG. 20 is an exploded side profile and perspective view of an illustrative fork portion in accordance with the present teachings.

DETAILED DESCRIPTION

Figure 1B:
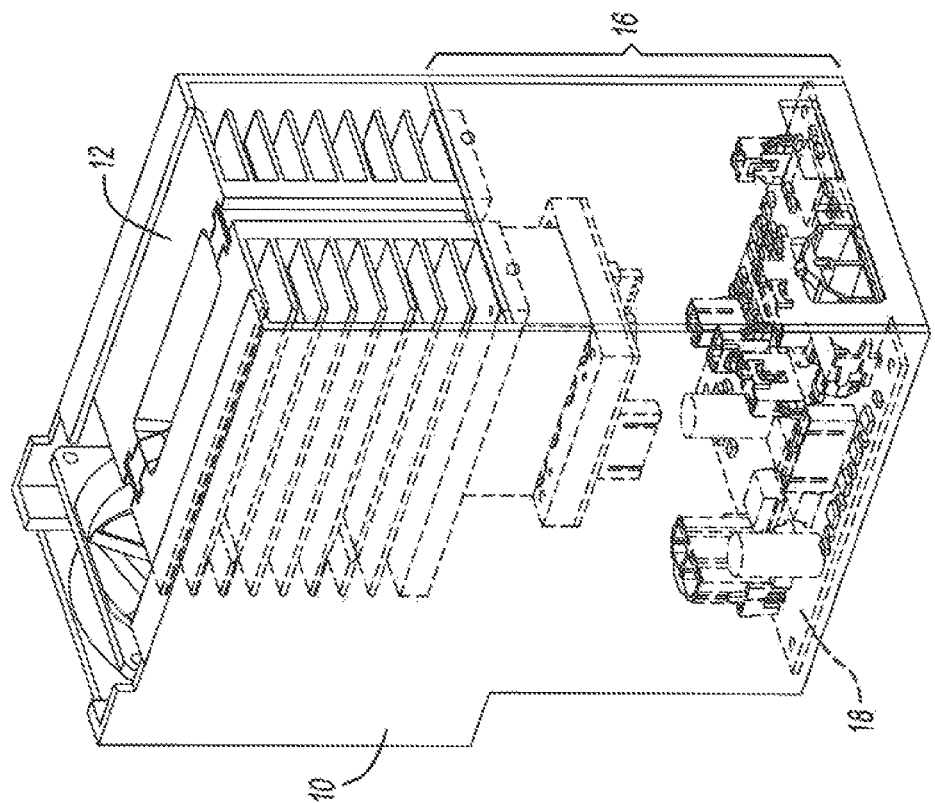
FIG. 1B is a view showing illustrative internal components of the module shown in FIG. 1A.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

This application is related to and claims the benefit of the filing dates of U.S. Provisional Application Nos. 61/681,879 filed Aug. 10, 2012 and 61/752,494, filed Jan. 15, 2013. This application is also related to U.S. application Ser. No. 13/484,963 filed May 31, 2012. The contents of the aforementioned applications are hereby incorporated by reference for all purposes.

The present teachings pertain generally to an improved device for performing high-speed real-time polymerase chain reaction. The device includes one or more PCR modules, each PCR module including one or more light sources, one or more detectors, one or more waveguide devices and optical componentry for light differentiation. Advantages of the instrument described herein include reduced componentry which allows for interchangeability of PCR modules and a reduced footprint. This includes the ability to employ less hardware per sample. Further, minimal hardware is required per sample such that the functionality of the components described herein is maximized over a wider number of samples. As a specific example, the instrument described herein may require only one light source (or one light source component) for multiple samples). Additional benefits provided in accordance with the teachings herein include that the optical detection portion is optionally free of moving parts (or moving samples) for increased reliability and fast multiplex detection. In addition, the present teachings provide for the emission and detection of multiple colors for multiplex PCR, and for the ability to give each fluorescent agent an intense specific light color that more closely matches the fluorescent agent's peak light absorption wavelengths. Further, detecting from the bottom of one or more samples as taught herein may leave side walls of the sample tubes available for maximum heat flow/thermal control and the top of the sample tubes available for simplified sample access. The multiple module arrangement of the present teachings also allows for on-demand instrument availability and increased sample throughput. The inclusion of multiple samples per module allows for each sample to be given a nearly identical thermal profile to better perform statistical comparisons of multiple samples.

The thermocycler instruments of the teachings herein follow the basic principles of WO/2009/105499 and U.S. application Ser. No. 12/918,594 (U.S. Publication No. 2011/0039305) and Ser. No. 13/484,963 in that a sample block (e.g., a sample holder) is sandwiched between opposing thermoelectric devices. The teachings, however, address a number of new features for thermocycler instruments that successfully and unexpectedly improve efficiency and operation of the instruments as compared with instruments that do not employ such features. The teachings further provide for thermocycler instruments that facilitate simultaneous amplification and quantification of nucleic acids.

The nature of the sample block being sandwiched between opposing thermoelectric devices indicates that samples located within the sample block receive light from a light source from either above or below the sample holder, given the difficulty with transmitting light through the thermoelectric devices. As a further result of the sandwich design, detection should preferably also occur from above or beneath the sample holder. It is also possible that the fiber optics may be integrated into the sample block in which excitation and/or emission light is transmitted through the side of the tube. It is also possible that apertures may be present within the thermoelectric devices such that the optical pathway for emission and/or detection occurs through these apertures.

The instrument thus includes a combination of components selected and adapted for relatively rapid cycling and real time quantification of nucleic acids. For example, the teachings herein contemplate use of instruments within the teachings for performing real-time nucleic acid amplification over a period less than about 40 minutes, less than about 30 minutes, less than about 20 minutes, or even less than about 15 minutes. The teachings herein contemplate that such amplification and quantification rates can be successfully employed for sample sizes of greater than about 2 microliters, 10 microliters, 30 microliters, 50 microliters, or even 70 microliters (e.g., a sample size of about 25 microliters). Relatively large yields of amplified nucleic acids (e.g., at least levels detectable by gel electrophoresis) are possible over a relatively short period of time. The unexpected ability to perform such rapid real-time amplification and quantification on relatively large sample sizes is one of the advantageous aspects of the present teachings. Aspects of the instrument also may be premised upon the recognition that thermal inertia characteristics of structures and materials used for thermocycler instruments can impede the rate at which thermal cycling can take place as may intrinsically occurring lags that occur due to electronic processing capabilities of an instrument. Accordingly, the present teachings also pertain, in various aspects, to unique approaches to addressing such obstacles.

The teachings herein envision the efficient operative employment of at least one first thermal cycling element for thermally cycling a sample in generally opposing relationship with at least one second thermal cycling element for thermally cycling the sample. Though other devices may be employed, the thermal cycling element for thermally cycling the sample typically will be one or more thermoelectric devices ("TEDs"). Thus, it is envisioned that a first TED and a second TED may be in generally opposing relation with one another. They may be generally identical and may be controlled to operate substantially identically with each other. A sample holder may be employed to carry a sample (e.g., a sample enclosed or otherwise carried within a sample container, such as a tube). The sample holder may be adapted to receive at least one sample (e.g., a sample carried in a sample container such as a tube) and to be disposed (e.g., in a sandwiching relationship) between the thermal cycling elements (e.g., between the first TED and the second TED). The sample holder may be adapted to receive a plurality of samples. Further, the thermocycling instrument may include a plurality of sample holders, each sample holder being located in thermal conducting relation with one or more thermal cycling elements. The thermal cycling elements may each include at least one heat exchanger (e.g., a suitable heat sink) for transferring heat relative from or to each of the cycling devices (e.g., the first and second TEDs).

The sample holder may be formed within a sample block, which may be a metallic sample block (e.g. heat block). The sample block may be a silver sample block. The heat block to house samples may be manufactured from rolled silver stock that has the oval bores formed by wire electrical discharge machining (EDM). An alternative manufacturing process such as a casting process or potentially splitting the block into two pieces for direct machining may also be used. Additionally, a slight increase in sample block thickness (e.g., an increase to about 3 mm) may improve temperature uniformity among the bores that receive the samples while having minimal impact on speed of the thermocycling.

As with other hardware components described herein, the above components may be configured and positioned in a way to afford efficient heat transfer to and from a sample. They may be configured and positioned in a way to help potentially reduce thermal inertia obstacles to efficient heating or cooling. They may be configured and positioned in a way to achieve substantially uniform heating or cooling rates to a plurality of samples that may be carried within the sample holder. Thus, the first TED and second TED may both operate to heat and/or cool one or more samples simultaneously in an effort to achieve a more uniform heating and/or cooling. They may be configured and positioned in a way to substantially account for the thermal phenomena of the components in executing temperature control.

To improve temperature control a fan may be included within the instrument. The fan may be a variable speed fan. The incorporation of a variable speed fan is advantageous in that it reduces audible noise and may also provide improvement to temperature uniformity at low fan speeds. Although, some PCR protocols may be run with no fan. The fan may be powered by a signal that is pulse width modulation (PWM) controlled. Thus, a fan may be selected that can handle a PWM power signal, or additional electronic circuitry may be added to modify a PWM signal into steady DC voltages.

The teachings envision the use of suitable temperature sensing componentry. For example, the componentry may be such that two or more sensors, which may include two or more sensors for each sample block, monitor (e.g., simultaneously and/or continuously) at least two temperature conditions, each originating in a location remotely of each other within the thermocycling device. For example, one sensor might sense a condition within the above-noted sample holder that approximates the temperature to which the sample is being subjected. That is, the temperature conditions are selected so that they can be relied upon as being related to (e.g., generally corresponding with in a direct manner) the temperature within the sample holder, which may be indicative of the temperature of a sample located within the sample holder. Another sensor might sense a temperature condition of a component, such as a heat exchanger, that provides useful information in accounting for the thermal inertia and thermal interactions during heating, cooling, and temperature holding. The componentry also is adapted to deliver information (e.g., via electrical signaling) corresponding with one or more sensed temperature conditions.

The teachings also contemplate a method (e.g., a computer-implemented method) for operating a thermocycler (such as the thermocyclers as described herein) for real-time amplifying and quantifying of nucleic acid (e.g., DNA (deoxyribonucleic acid)) of a sample (e.g., a patient sample, such as a human patient sample). The method may include obtaining user input such as in the design of a desired PCR protocol. The method may include a step of displaying one or more user interfaces. Such user interfaces may be configured so that a user is able to input operational instruction protocol information for operating the thermocycler. Such instruction information may be selected from one or any combination of at least one temperature setting, number of cycles to be performed, times for one or more cycles, hold times at one or more temperatures, or the like. The method may include a step of receiving user operational instruction protocol information inputted by the user. The method may include a step of causing the thermocycler to execute a protocol for nucleic acid amplification and/or quantification on the basis of the operational instruction protocol information inputted by the user. The method may include a step of storing (e.g., in a suitable memory device in communication with the instrument) operational instruction protocol information inputted by the user. The method may include a step of displaying for a user previously programmed operational instruction protocol information so that the user can modify such information for designing a protocol. The method may include a step of receiving information about a temperature condition to which a sample is being subjected and causing such information to be displayed to a user substantially in real time. The method may include a step of providing a user with an opportunity to start, stop and/or pause a protocol during execution of such protocol on a sample. The method may include a step of outputting data about an actual or proposed protocol. The method may include one or any combination of other steps of storing notes inputted by a user, providing a preview of a protocol before causing a thermocycler to execute the protocol, or performing a diagnostic check to ascertain operability of a thermocycler.

The method may include a step of receiving optical input parameters from the user which includes one or more of the following: the PCR cycles in which to perform an optical read, the fluorescing which are being used for the optical detection, the color wavebands to use to excite the fluorescing agent, the color wavebands to use to detect the fluorescing agent, the sample identification, the sample type (no sample, known standard, unknown sample, positive control sample, negative control sample, or no DNA template control sample), the DNA template quantity of known standards and/or controls, and melting curve information including temperature start, temperature stop, and melting curve resolution. The method may include a step of storing the optical input parameters. The method may include a step of retrieving stored optical input parameters. The method may include a step of displaying optical detection data which includes one or more of the following: compatibility of user-selected fluorescing agents, estimated quantification threshold (e.g. the fractional cycle number at which the amplified DNA is detectable from the background noise), estimated initial DNA copy number for unknown samples, estimated meting temperature of the detected DNA. The method may include a step of graphing the optical detection data which includes one or more of the following: a graph of the optical signal as a function of PCR cycle number, a graph of the optical signal as a function of sample or sample-holder temperature, a graph of the negative slope of the optical intensity with respect to temperature as a function of temperature, a graph of the actual and/or expected optical data as a function of wavelength. The method may include a step of storing the optical data. The method may include a step of retrieving stored optical data. The method may include a step of applying the temperature and/or optical input to one or more modules independently or simultaneously. The method may include a step of displaying, storing, or retrieving stored data from one or more modules. The method may include a step of obtaining temperature and optical input from a barcode scanner, 2D barcode scanner, NFC (near field communications), or RFID (radio frequency identification) from an appropriate test kit, assay, or sample tube.

The teachings herein also contemplate a non-transitory computer readable medium comprising program instructions for performing the methods (or any of the steps) as described in the herein. The teachings thus envision at least one computer software or firmware program including code that provides instructions to hardware for performing PCR which, when executed by a suitable electronic processor or other computer processor, performs the methods (or any of the steps) as described in the herein. The teachings also contemplate a system for performing a PCR amplification reaction the system comprising a device including a memory storage medium for implementing the program instructions of the non-transitory computer-readable medium. The memory storage medium may be on a computer (e.g., a computer having a processor with a processing speed of at least about 1.67 GHz, such as an Inspiron Mini 1018, from Dell). The computer may be external and attached to the instrument. The computer may be internal to the instrument (e.g. an industrial mini-ITX based computer with extended life cycle such as a J&W ITX-IC2M1026S (available from J&W, South San Francisco, Calif.) dual core atom mini-ITX mainboard) with a display unit (e.g. a screen or a touchscreen) internal to the instrument or a port for attaching an external monitor. The computer may employ a Windows®-based operating system, or some other like system. The system may include a thermocycler in accordance with the present teachings, one or more devices for collecting information about the temperature condition of the sample holder, and an output device for displaying data obtained or generated by the analyzing device. The output device may be a display panel associated with the computer. Multiple functions of the software may be caused to be performed by code on a single non-transitory storage medium, or on multiple media. For example, functions may reside on firmware associated with a controller that is on-board the thermocycler instrument.

The instrument of the present teachings may require the use of a specialized tube for facilitating qPCR (quantitative real time polymerase chain reaction) that facilitates transfer of light. The tube preferably allows for detecting the emission of light from fluorescent dyes/probes within the tube. The amount of light detected is generally proportional to the amount of formed PCR product, resulting in simultaneous PCR-based amplification and detection. Preferably, the tube (or at least a portion thereof) is optically clear for high transfer of light to/from a reaction mixture within the tube with at least about 50% transparency (and preferably at least about 80% transparency) to the visible light spectrum.

As an example, an optically clear resin may be used and injection-molded to form the entire tube. An exemplary polypropylene resin is a cyclic olefin copolymer resin from TOPAS Advanced Polymers, sold under the trade name 5013S-04. Another exemplary polypropylene resin is a clarified, high-melt random copolymer from LyondellBasell Industries, sold under the trade name Pro-fax RP448S. These resins exhibit high flowability to fill thin-walled areas of the tube while providing high transparency.

As a further example, the tube may be optically transparent only in portions of the tube in which the light excitation and emission occurs. Both excitation and emission may be performed through the bottom of the tube and thus only the bottom tip of the tube need be optically clear. As such, a two-shot mold process may be used to create a bottom portion comprised primarily of an optically clear resin with the rest of the tube may comprise a second, different resin that is not necessarily optically clear.

Figure 17A:
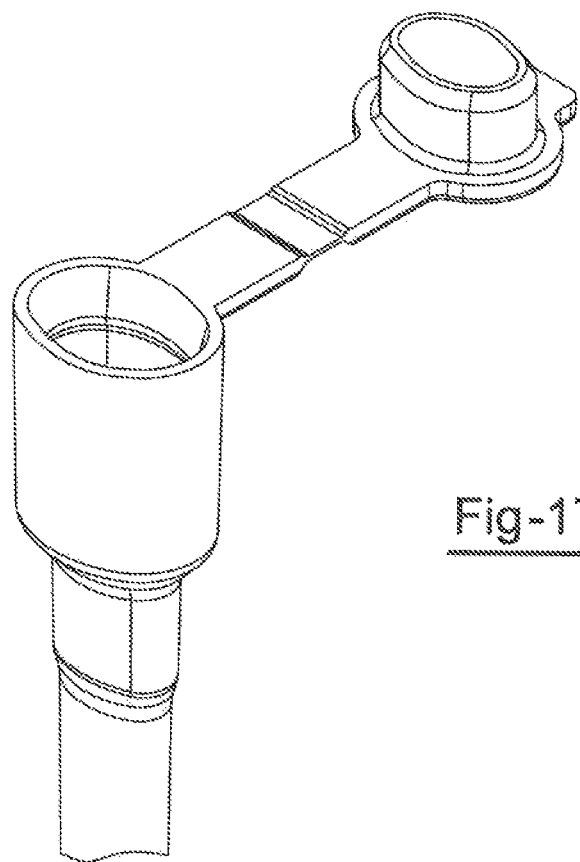
FIG. 17A is perspective view of an illustrative tube and cap in accordance with the present teachings.
Figure 17B:
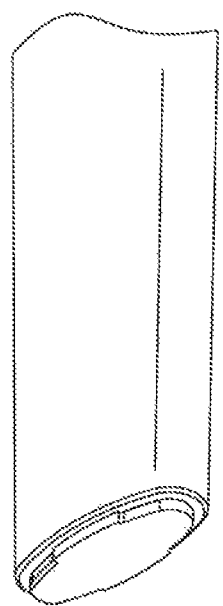
FIG. 17B is perspective view of an illustrative tube having an optically clear bottom portion in accordance with the present teachings.

An over-molding technique may also be used to construct an optically clear portion of the tube. By way of example, an optically clear bottom piece may be over-molded during the tube fabrication process (see FIG. 17B). The optically clear piece may be introduced into the mold cavity prior to injection of a polymeric material. The optically clear portion may be flat to minimize light reflection, light distortion, and light absorption by the sample tube. The optically clear portion may be a lens shaped plastic, glass, fiber-optic cable, or the like. The optically clear portion may also serve to stabilize the core-pin of the injection molding process to minimize core pin deflection.

Alternatively, a secondary external operation may be utilized to form an optically clear portion of the tube. By way of example, the tube may be molded with an open end to which an optically clear piece is then inserted. Fusion between the tube and the optically clear piece may be achieved by thermal bonding, adhesive bonding, mechanical fitment, or other means as known in the art of plastics bonding and manufacturing.

One or more optically clear portions of the tube may take on specific dimensions and curvatures (i.e. lens design) to achieve optimal coupling (i.e. transmission, dispersion, and focusing of light) among the sample fluid, the excitation means, and the detection means. The optically clear portions may be comprised of planar, concave, convex, meniscus, Fresnel, or other lens surfaces as known in the art of optics. In a preferred embodiment, the shape of the optical pathway of the bottom of the tube may be comprised of two substantially parallel planar surfaces with a relatively thin wall thickness. A high degree of polish of the optical pathway surfaces is also advantageous to light transmission.

The one or more optically clear portions may be formed on the bottom of the tube. Alternatively, the one or more optically clear portions may be formed along the top of the tube. The top of the tube (i.e. cap) may be optically clear in embodiments in which excitation, emission, or both occur above a sample fluid (see FIG. 17A). In one embodiment, the light source may be located above the sample fluid while the detection means is located below the tube, such that the tube may include more than one optically clear portion. In another embodiment, both the light source and detection means are located above the tube such that transmission of light necessary to conduct real-time PCR occurs through the cap.

As mentioned above, a light source may be utilized within the instrument. The light source may be located within the instrument such that it provides light through one or more optically clear portions of a tube in which a sample is located. The light source may be located on a printed circuit board. The printed circuit board may thus provide an electrical supply to the light source. The light source may include one or more light emitting diodes (LEDs). In the event that the instrument contains more than one sample block, each sample block may include its own light source. Each sample block may have multiple light sources, with one or more light sources for each sample well or a shared light source among wells (e.g. one light source optically connected to two or more sample wells). Each light source may be carried on a common substrate. Further, each light source may include a plurality of distinct lights such that each distinct light provides light at a different wavelength. As an example, each sample block may include an array of LED lights, each array including distinct lights at one, two, three, four, or more different wavelengths in order to better match the peak optical absorption wavelengths of various fluorescent agents. In this case, the LED light sources may be grouped underneath a fiberoptic waveguide such that one or more light sources enter the same fiber optic fork. Alternatively, the LED's may be grouped together on the same common substrate (i.e. a compact printed circuit board or assembly), but with each LED positioned beneath its own fiber optic fork. A plurality of high power LEDs (of wavelengths typically covering the 400 nm to 700 nm visible light region) may be grouped together in an area less than about 3 mm by 4 mm (an example of which is available from Philips Lumileds Lighting Company under the designation Luxeon Z). One such grouping may include four Luxeon Z LEDs with wavelength peaks of approximately 477.5 nm, 522.5 nm, 585.5 nm, and 665.0 nm. A second such grouping may include four Luxeon Z LEDs with wavelength peaks of approximately 447.5 nm, 494.0 nm, 537.5 nm, and 635.0 nm. Two or more such groupings may be incorporated in each module with each grouping having its own fork of the fiber optics waveguide and optionally its own multi-band bandpass filter.

Alternatively the grouping may include seven Luxeon Z LEDs which are staggered to form a hexagonal shape and include up to seven colors with wavelength peaks selected from the following list: 442.5 nm, 447.5 nm, 452.5 nm, 457.5 nm, 462.5 nm, 467.5 nm, 472.5 nm, 477.5 nm, 494 nm, 503 nm, 522.5 nm, 527.5 nm, 532.5 nm 537.5 nm, 585.5 nm, 588.5 nm, 591 nm, 593.5 nm, 615 nm, 625 nm, 635 nm, 655 nm, or 665 nm. A grouping of seven LEDs staggered to form a hexagonal shape may include wavelength peaks of approximately 477.5 nm, 494 nm, 522.5 nm, 537.5 nm, 585.5 nm, 635 nm, and 665 nm. The groupings of LEDs may have a lens to focus light through one or more filters and/or into one or more fiber optic excitation forks. The lens may be an array of individual lenses or it may be a single unit with multiple integrated lenses, one for each LED. Alternatively, each LED light source may include only 1 distinct light adapted to emit a plurality of different wavelengths. In this case, a plurality of LEDs (each of a different peak wavelength) may be encapsulated behind a single lens within a single assembly (an example of which is available from LED ENGIN, Inc., under the designation LZ4-00MA00). Each compact grouping or single assembly of LEDs may be considered as a light emitting diode device. As alternatives to light emitting diodes, white light sources such as halogen or tungsten bulbs or lamps, laser light sources, or other excitation means may be employed.

The light source may be part of an assembly that includes a carrier having a first surface and a generally opposing second surface. The light emitting diode may be exposed via the first surface. One or more electrical contacts (e.g., pads) may be located on or as part of the second surface and be in electrical communication with the diode. In this manner, the pads may be applied to a substrate (e.g., by way of a soldering to a printed circuit board). The upper surface may include one or more apertures through which the light may be emitted from the LEDs. The upper surface may include one or more conduits of a predetermined depth (e.g. about 1 mm, 2 mm, 3 mm, 4 mm, 5 mm or higher) that may be suitably adapted to connect in light transmission relationship with a wave guide structure (e.g., a fiber optic structure). The conduits may be elongated and include a longitudinal axis. They may be generally cylindrical. They may be at least partially conical. They may include a generally round, oval, triangular, rectangular or other polygonal cross-sectional profile relative to the longitudinal axis. They may have a wall structure defining a passage in the conduit that has a taper (e.g., less than about 15, 10, or even 5°, though tapers of at least 20, 30 or 45° are possible) relative to the longitudinal axis.

The light source will typically include an exposed end through which light is emitted. For each light source of a predetermined wavelength, the end may have an area that is smaller than about 9 $mm^2$, 6 $mm^2$, or even 3 $mm^2$. It may have an area that is larger than about 0.5 $mm^2$, 1 $mm^2$, or even 2 $mm^2$. The emitted beam may have an emission axis, and may exhibit a generally linear, rectangular, oval, circular, or other cross-sectional profile relative to the emission axis.

The light source may exhibit one or any combination of performance characteristic as set forth in the LUXEON Z Datasheet DS105 20120916, incorporated by reference herein (without limitation, pages 3 through 9, page 14-20, and 24 through 27). The light source may exhibit one or any combination of structural characteristic as set forth in the LUXEON Z Datasheet DS105 20120916, incorporated by reference herein (without limitation, pages 10 through 13 and 21 through 23).

The light source may be a relatively high power light source which may provide for more sensitive detection capability. As an example, the light source may be rated at 40 Watts or more, although the light source may or may not be operated at the maximum level. As a result of the high power of the light source, it may be capable of dissipating heat. The light source may thus be in close thermal communication with a heat sink, which may be located onto the printed circuit board. The heat sink may be located beneath, and/or around, the light source. The heat sink may assist in dissipating heat from the light source.

An additional benefit of LEDs is that they use less power than other types of light sources (e.g., compact fluorescent or incandescent bulbs) per unit of light generated. LEDs also have improved durability as compared to other light sources. In addition, the use of LEDs as the light source allows for compact packaging for insertion into small spaces within the instrument. Preferably the packaging for the light source may be less than 3 cm on each side, or less than 1 cm on each side, or even less than 0.8 cm on each side or a grouping of LEDs with the grouping being less than 1 cm on each side, or even less than 4 mm on each side. As a result, LEDs allow for effective output and performance from a device that occupies minimal space. In one embodiment, the light source can be located beneath the heat exchangers. In an alternative embodiment, the light source may be located above the sample block. In the event that the fiber optics are flexible, the light source may be located anywhere depending upon the arrangement of the samples and the nature of the tubes containing the samples. The small packaging of the light source assists in maintaining the small, lightweight and portable nature of the instrument.

The selected light source should be compact, compatible with a fiber optics design, and sufficiently bright. In the event that LEDs are selected as the light source, it may be beneficial for multiple LED elements to be located into a single housing. For example, a single housing may include at least 4, at least 5, at least 8, or even at least 12 LED elements such as the LuxiGen family of LEDs available from LED Engin, San Jose, Calif. Any LED lens may be formed with a flat top for improved connection to any fiber optic cable. Ultra-small LEDs may be utilized such as Luxeon Z LEDs, Phillips Lumileds Lighting Company, San Jose, Calif. or XLamp LEDs from Cree, Morrisville, N.C. These ultra-small LED's may be compactly grouped together. A four-color LED grouping may be utilized as the light source. A seven-color LED grouping in a hexagonal shape may be utilized as the light source with seven distinct colors. A seven-color LED grouping in a hexagonal shape may be utilized as the light source with five distinct colors and one or two colors repeated for additional light intensity of that specific color and/or additional lifespan by switching from one LED of a specific color to another LED of that same color. An eight-color LED combination may be utilized as the light source.

The instrument may also include a device for detecting a reaction within a sample. The detector may include a photodiode array which issues a signal proportionally based upon intensity of light it receives. An example of a photodiode is the Taos TSL 1402R, available from AMS-TAOS USA Inc., Piano, Tex. The detector may be located within less than about 10 mm, less than about 5 mm, or even less than about 3 mm from an end of a waveguide to help avoid light from becoming diffuse. The detector may be located in an isolated contained chamber so that it is not exposed to any other light source and is insulated from heat generated by the rest of the instrument. The chamber may be formed as a surrounding wall structure that substantially insulates the detector from other light. The detector may be formed as an individual array for each sample or alternatively may be a single array subdivided into array portions that are dedicated to individual samples. The detector may be formed as arrays arranged in elongated thin strips so that pixels of the arrays are aligned end to end. Each elongated strip may include from about 25 to about 200 pixels (each being about 65 microns by 55 microns). The detector may be a two-dimensional array of pixels such as with complementary metal-oxide-semiconductor (CMOS) or charge-coupled device (CCD) detector circuitry. Alternatively the photodiode array may consist of several larger individual photodiode elements (about 1 mm×1 mm, or about 3 mm×3 mm) each with one pixel per detection color. Alternatively, PIN (p-type, intrinsic and n-type semiconductor regions) photodiodes may be employed and may be present with one PIN photodiode per sample, multiple PIN photodiodes per sample, or one PIN photodiode shared by multiple samples. An array of the PIN photodiodes may exist for each sample in situations where each PIN photodiode is paired with a bandpass filter of a specific wavelength. For instances in which one PIN photodiode is used per sample, a lens may be used which directs light from at least one bandpass filter to the single PIN photodiode. For instances in which one PIN photodiode is used by multiple samples, a lens may be used which directs light from at least one sample to the PIN photodiode.

Each array may monitor one, two, three, or more samples at a time. Each array may be adapted for moving from sample to sample. The arrays may be arranged to read more than one pixel at a time (from more than one sample). The time between the readings may affect sensitivity due to the entry of light. It may thus be desirable to complete readings as quickly as possible (e.g., less than about 0.5 milliseconds average per pixel per reading) to maximize sensitivity. It may be desirable to complete readings for each pixel in less than 0.1 second, or even less than 0.01 seconds. A sum of reads for each pixel may be used to result in a total read value per specified integration time. It may be desirable to complete the total reads of all samples for all dyes in less than 10 seconds, less than 5 seconds, or even less than 3 seconds to maintain minimal run times of the instrument.

In another embodiment, the photodiode array may simply be a grouping of individual photodiodes. In this case, unique bandpass filters may be positioned above each photodiode such that the signal from that photodiode is related to a specific fluorescent agent. In yet another embodiment, a single photodiode (e.g. PIN photodiode) is used for detection of all fluorescent agents. In this case, different bandpass filters may be moved into position above the photodiode (e.g. a filter wheel or shuttle) so that the signal generated at a specific time corresponds to a fluorescent agent. This allows for detection of multiple fluorescent agents by cycling through the filters during a detection step. Alternatively, a stationary multi-band bandpass filter may be employed above the photodiode such that the light detected corresponds to a certain fluorescent agent, dictated by the excitation wavelength provided at that instance.

Alternatively, the detector may include at least one spectrometer which may also require the use of a prism device or optical diffraction grating to separate light according to different wavelengths. The detector may also include at least one charge-coupled device or other capacitor containing device or photomultiplier tube.

The ability to excite one or more probes contained within a sample for testing may be enhanced by employing one or more features for controlling the light that is directed to the sample holder from one or more light sources. For example, without limitation, as to light from one or more light source, one or more features may be employed to attenuate, intensify, modulate, collimate, refract, reflect, diffract, or filter such light or any combination of the foregoing.

Consistent with the foregoing, the ability to detect light from one or more excited probes contained within a sample may be enhanced by employing one or more features for controlling the light that is emitted from the sample (or at least one probe therein). For example, without limitation, as to light from a sample, one or more features may be employed to attenuate, intensify, modulate, collimate, refract, reflect, diffract, or filter such light or any combination of the foregoing.

An approach that may be employed for enhancing transmission of light for excitation of one or more probe, for detecting fluorescence emitted by one more probe or both may involve the selection of a suitable filter arrangement. One or a combination of two or more filters may be employed for this purpose. Selection of a fitter for this purpose may be based upon one or more desired attribute of the filter.

In the context of detecting light, it may be expected in some instances that a filter is selected by which a significant amount of light of one or more predetermined wavelengths is allowed transmission through the filter for affording a larger amount of detectable light for a detector. For example, it may be possible that one or more absorptive filter is employed, such as a filter with an optical density (OD) value of about 4, 3, 2, 1 or lower. Successful results may be achieved by the use of one or more filters having an OD value of greater than 4 (e.g., a value of OD 5, OD 6, or OD 7). The cumulative OD value of such filters may be greater than 4 (e.g., a value of OD 5, OD 6, or OD7). The OD values are based upon transmission values measured at a wavelength from about 400 nm to about 800 nm in accordance with a spectrometer according to standard optical metrology transmission measurement techniques (often a custom modified spectrometer is used to measure large optical densities, over about OD 4, and to measure filters with sharp transitions in optical density as a function of wavelength).

The filters may be present on the LED waveguide fork, the detection waveguide fork, or both. The filters may be separate components or the filters may be deposited directly onto lenses, LEDs, photodiode detector devices, and/or fiber optic waveguides.

The filters may be neutral density filters. They may be uncoated. They may be metallic coated. They may be made of optical quality glass, UV-grade quartz or some other suitable material.

One or more interference filters may be employed for selectively allowing transmission of light within one or more predetermined range of wavelengths, while reflecting light of other wavelengths. For example, one or more dichroic filters may be employed. Examples of suitable dichroic filters may exhibit one or more performance characteristics including transmitting light from the LEDs at the excitation wavelength range(s), and reflecting light at the fluorophore emission wavelength range(s) (or the reverse of reflecting the excitation light and transmitting the emitted light). An example of a suitable dichroic filter employed herein is commercially available from Edmund Optics, Barrington, N.J. under the designation #67-055.

One of more filters may be employed at one or more locations within a system. One or more filters may be employed between a source of light and a waveguide (e.g., a fiber optic structure) through which the light is transmitted. One or more filter may be employed between a light emitting portion of the waveguide (e.g., fiber optic structure) and the sample (and/or holder within which the sample is contained). One or more filter may be employed between the sample (and/or holder within which the sample is contained) and any detector.

One or more components of the system may have a filter assembled to it. One approach may be to select materials for the sample holders of the system herein by which the material intrinsically filters one or more predetermined wavelength or range of wavelengths.

One example of a filter that may be employed herein is a linear variable fitter. For example, such a filter may be employed in advance of a detector of the system. Another option that may be employed alone or in combination with a linear variable filter may be to employ one or more bandpass filters or other filter. Examples of suitable bandpass filters may exhibit one or more performance characteristics including a hard coating, at least 90% transmission in the bandpass wavelength range, an optical density of at least OD5 in the blocking wavelength ranges, a transmission band of approximately 10 nm to 50 nm, and a sharp transition (less than about 5 nm) between the transmitting wavelengths and the blocked wavelengths. Example of a suitable bandpass filter employed herein is commercially available from Edmund Optics, Barrington, N.J. under the designation 67-013.

Any linear variable filter may be utilized for filtering light such that only light having certain wavelengths can pass through the filter at different filter locations. As a result, only light of a known wavelength may pass through the filter and to the detector (e.g., specific pixels of an array) so that the light that is passing through is a predetermined known wavelength for which only intensity needs to be measured for each pixel in the detector. Examples of suitable linear variable filters may exhibit one or more performance characteristics including a hard-coating, separation of light into a spectral range from about 450 nm to about 800 nm, average transmission of over 40%, and an optical density of at least OD3. Examples of suitable linear variable filters employed herein are commercially available from Delta. Hørsholm, Denmark under the designation LF102155 or JDS Uniphase, Santa Rosa, Calif. under the designation 30119150. The fitter may be substantially similar in size to the detector. The filter may be located onto a support with the detector or may be located on a separate support from the detector. The filter may be permanently adhered to the detector with optically transparent adhesives so that there is a precise and repeatable relationship between the wavelength and pixel number. While typically the transmitted wavelengths will vary linearly across the linear variable filter, other monotonic functions (e.g. logarithmic) may be utilized.

As an alternative to the linear variable filter, a series of discrete bandpass filters may be employed. The series of bandpass filters may include distinct filters grouped together or an integrated assembly in which various portions of a substrate represent different bandpass characteristics. The bandpass filters may be lined in parallel so that the assembly aligns optically with the detector pixels or photodiodes. In this respect, this embodiment can be simply viewed as a linear variable filter with discrete step-wise portions rather than continuously variable. Alternatively, a multi-band bandpass filter may be used in conjunction with the detector. In this case, the wavelength of light transmitting through the multi-band bandpass filter to the detector is related to the excitation light provided at that instance based upon the excitation/emission behavior of the fluorescent agent. The discrete bandpass or multi-band bandpass filters may be arranged in a fixed position generally with one filter per LED or photodiode detector device. The discrete bandpass or multi-band bandpass filters may be arranged on a filter-wheel which moves the excitation and/or detection filters between the LED and fiber optics and/or between the fiber optics and the photodiode detector device.

Another example of a filter system would be a series of dichroric beamsplitters, dichroric filters, dichroric mirrors, and/or dichroric prisms which reflect light of certain wavelength ranges at an approximately 90° angle to the incoming light and the reflected colored light branches then pass through a series of suitable bandpass filters located over a detector device. In this latter example, the incoming beam of light is split into one or more different colored light branches by passing through or being reflected by the series of dichroric beamsplitters. The series of bandpass filters further filter the colored light branches into specific wavelength ranges. Each bandpass filter is located over a known number of photodiode elements in a photodiode array and/or individual photodiodes in a compact group of photodiodes within the detector device. Thus, the intensity of light of each colored light branch can be measured simultaneously with no moving parts. An example of a suitable colored light branch detection device is the OptoFlash Optical Engines from Newport Corporation. Franklin, Mass. One or more optical fibers can be used within the same OptoFlash, and thus multiple sample tubes can be analyzed sequentially by exciting each sample tube sequentially with light. A custom OptoFlash may be used with filtered color light branches with light wavelength ranges of approximately 510 nm to 547 nm; 555 nm to 565 nm; 565 nm to 575 nm; 575 nm to 600 nm; 608 nm to 655 nm; 665 nm to 691 nm; and 699 to 770 nm. Additional color light branches could be added to the OptoFlash to detect additional wavelength ranges or fewer color light branches. The color light branch wavelengths could be adjusted to be more suited for different fluorescing agents with the color light branch bandwidth being used to control sensitivity and to control the total number of different fluorescing agents that will be detected.

The employment of one or more suitable waveguide structures may be employed as discussed herein. One particular approach is to employ a fiber optic structure. Though it may be believed that the selection and employment of a suitable fiber optic structure is readily within the skill in the art, experience is believed to prove the contrary. Without intending to be bound by theory, it is believed that the selection of a suitable optical fiber structure may not be readily predictable. By way of example, it is possible that certain applications may seek to employ a fiber optic structure having a relatively large numerical aperture value (e.g., greater than about 0.55, 0.65 or even 0.75). This may be a sensible approach both for assuring a relatively large transmission of light for excitation, a relatively large angle of light acceptance (e.g., at least about 33°) or both. However, for sensitivities desired for certain of the applications herein, such structure may actually lead to less efficient performance in the way of light transmission and/or detection. Thus, the teachings herein contemplate the employment of fiber optic structures that have a numerical aperture value that is less than about 0.52, 0.50, 0.45, 0.40 or smaller (e.g., to as low as about 0.5).

The structure may be configured so that the angle of light acceptance may also be a value that is below about 32%, 30%, 25%, 20% or lower. It may be an angle of 5%, 10% or higher. The angle of incidence is measured as the angle between the normal surface (of the terminal end of the optical fibers) and the incident light ray.

It will be recognized that numerical aperture values refer generally to a maximum angle at which a particular fiber can accept the light that will be transmitted through it. The numerical aperture value of an optical fiber is thus correlated with the size of a cone of light that can be coupled into its core. As the skilled artisan will appreciate, a value for numerical aperture can be derived by calculating the sine of a half angle of acceptance within a cone of light that enters a core of a fiber. An approach to measure numerical aperture is illustrated in TIA Fiber Optic Test Procedure FOTP-177 (Method A) Numerical Aperture Measurement of Graded-index Fiber.

The waveguide may be a bifurcated waveguide such that it includes a first and second fork portion. The first fork portion may extend between the sample holder and the light source (e.g., an LED device) for transmitting light emitted from the light source to the sample contained in the sample holder to excite a fluorescing agent. The second fork portion may extend between the sample holder and the detector (e.g., a photodiode detector device) for transmitting light emitted by the fluorescing agent upon its excitation and having a first end that is proximate the sample holder and a second end that is proximate the detector. The waveguide may be formed of a single structure or may be formed of optical fiber bundles. The waveguide or waveguide fibers may be formed of a polymeric or glass material. The waveguide or waveguide fibers may be made of single-mode optical fibers or multi-mode optical fibers, or any combination thereof. The waveguide may have the optical filters (bandpass filters and/or linear variable filters) or lenses directly deposited on the terminal ends.

The waveguide may be a multi-branched waveguide such that it includes at least one excitation fork portion (e.g., a first fork portion) and at least one emission fork portion (e.g., a second fork portion). The waveguide may include at least two, at least three, at least four, at least five, or more excitation fork portions. The number of excitation fork portions may be the same as the number of LED's present in the light emitting diode device. The excitation fork portion end proximate the end of a light source may branch out to provide light to one, two, four, eight, or more samples. The waveguide may include at least two, at least three, at least four, at leave five, or more emission fork portions. The number of emission fork portions may be the same as the number of detector wavelength ranges. The at least one emission fork portion proximate a sample may branch out to different detector portions. The at least one emission fork portion proximate a detector or detector portion may branch out to provide detection of at least one, two, four, eight, or more samples. In embodiments in which the excitation occurs from above the samples, the waveguide positioned below the samples may be void of excitation fork portions with only emission fork portions present.

The waveguide may be arranged so that a terminal end interfaces with the detector and will be elongated to coincide with the elongated structure of an array as discussed above. The instrument may include a manifold assembly that connects with the printed circuit board that carries the light source (e.g., the LEDs), and includes passages. These passages may allow for isolation of the individual light source assemblies and may be adapted to receive the waveguide (e.g., fiber bundles).

The instrument may include a housing for receiving the waveguide. The housing may include an upper portion that is adapted to fit in between the heat exchangers and to be aligned with (and located below) a sample holder. The waveguide may partially extend into the wells of the sample holder for close coupling and alignment of the waveguide to the sample tube. The housing may include one or more projections for aiding in aligning the housing within the instrument. The housing may also include one or more mounting flanges to provide a surface for attaching to a cavity within the instrument. The housing may further include a base portion having a cavity defined therein through which one or both fork portions of the bifurcated waveguide (e.g., fiber optic bundles) are passed, and which can receive a resin for potting the waveguide. The housing may also include one or more cover portions. A bottom cover portion may be adapted to interface with the detector and may be located above the printed circuit board and light source located thereon. One or more ports may also be formed along a surface of the housing so that the one or more ports align with the light source. The light source may penetrate through the ports or alternatively may remain adjacent to the ports without penetrating the ports. There may be an optical filter (such as a bandpass filter) between the light source and the penetrating ports.

The detector may be adapted to receive light from a plurality of sources. For example, the detector may receive (e.g., detect) light from a fluorescing sample and light reflected from the light source. Multiple fluorescing agents with different emission wavelengths may be present in the sample. As such, it may be necessary for the detector to be capable of differentiating different colors (e.g., light emanating from different sources and fluorescing agents) so that the software can differentiate data obtained from the fluorescing sample. As a result, it may be beneficial to include a filter such as a bandpass filter. Alternatively, a prism device or optical diffusion grating may be utilized for prismatic separation of the light (which may require detectors that will detect the difference between the light from one or more fluorescing agents and the light from the light source so that data from each can be separated).

As mentioned above, one possible approach is to employ a plural band bandpass filter. A plural band (in other words, multi-band) bandpass filter may be employed in conjunction with either or both the light source or detector. The band amount can be selected to correspond generally with the number of light sources of different wavelengths used for excitation of a sample, or the number of different detection wavelengths desired. For example, the employment of an excitation quad-band bandpass filter (if a four light source is employed) may be advantageous. Alternatively, dual-band or tri-band bandpass filters may be partially employed to minimize the number of components as compared to a design using single-band bandpass filters. Such a multi-band bandpass filter may suitably be employed. Such a filter may be sized to be within a predetermined size (e.g., covering an area that is only a portion of the total area of the array that defines the detector). For example, a detector may include an array of a predetermined number of pixels adapted for detection. However, the filter may be sized for allowing transmission of light to only a fraction of the pixels (e.g., less than about 75%, less than about 50%, less than about 25%, less than about 10% or even less than about 5% of the pixels) available for detection.

As also discussed above, the light source selected may include groupings of two or more, preferably at least four, LEDs for ease of providing equal light into a fiber optic cable and ease of printed circuit board design. In addition, one or more light source bandpass filters may be utilized. Preferably, multi-band bandpass filters, more preferably quad band bandpass filters, may be utilized. The multi-band bandpass filters may be hard-coated for maximal resistance to heat and humidity. The multi-band bandpass filters may be adapted to allow light in certain wavelength regions to reach the PCR samples for fluorescent dye/probe excitation but block wavelength regions where those fluorescent dyes/probes emit light to maximize the signal-to-noise ratio in the detection signal. For example, the multi-band bandpass filters may be a quad-band bandpass filter which is hard-coated to allow light with at least 80% transmission (or even greater than 95% transmission) in the 460 nm to 500 nm region, the 510 nm to 535 nm region, the 570 nm to 590 nm region, and the 640 nm to 690 nm region while allowing less than 1% transmission, less than 0.1% transmission, or even less than 0.01% transmission in the rest of the visible wavelength spectrum. The optical density of that filter in the transmission regions could be 0.25, 0.1, 0.05, 0.02, 0.01 or lower. The optical density between the transmission regions could be 3, 4, 5, or even 6 or higher. A second hard-coated quad-band bandpass filter may allow light with at least 80% transmission (or even greater than 95% transmission) in the 405 nm to 460 nm region, the 485 nm to 510 nm region, the 535 nm to 565 nm region, and the 610 nm to 650 nm region while allowing less than 1% transmission, less than 0.1% transmission, or even less than 0.01% transmission in the rest of the visible wavelength spectrum. The optical density of that second filter in the transmission regions could be 0.25, 0.1, 0.05, 0.02, 0.01 or lower. The optical density between the transmission regions could be 3, 4, 5, or even 6 or higher. It will be apparent to those of skill in the art that slight variations (up to about 5 nm or even 10 nm) in wavelength cutoffs of the multi-bandpass filters would still be acceptable for exciting florescent dyes/probes or that any of the transmission regions in the above quad-band filters could be swapped in any combination without any harm to the performance of the optical detection system. Such quad-band bandpass filters can be custom manufactured by any number of companies such as Omega Optical, Inc., Brattleboro, Vt.; Evaporated Coatings, Inc, Willow Grove, Pa.; or Delta, Copenhagen, Denmark.

Preferably, the instrument is capable of providing for at least four excitation colors for each sample and is further capable of detecting at least four emission colors from each sample (see Table 1 for a short list of commonly used dyes/probes). As shown in Table 1, only approximate peak wavelengths are listed, but the reporter dyes/probes can be used outside that wavelength range, albeit less efficiently. The most commonly used fluorescing agents require blue (480 nm to 495 nm), green (520 nm to 550 nm), amber (585 nm to 615 nm), and red (640 nm to 660 nm) excitation light. It is expected that the real-time optical detection be capable of producing light at or quite near those four wavelengths. A five or six color instrument would be preferred.

Table 1

TABLE 1

Commonly used fluorescing agents, their excitation wavelength peaks, and their emission wavelength peeks. Generally, real-time PCR will function if the cycler can emit and detect within ±10 nm to 20 nm of the peak.

| Fluorescing Agent | Excitation/Absorption Peak (nm) | Emission/Detection Peak (nm) |
|---|---|---|
| AMCA | 353 (violet) | 442 (indigo) |
| Cyan 500 | 450 (indigo) | 500 (blue green) |

TABLE 1-continued

Commonly used fluorescing agents, their excitation wavelength peaks, and their emission wavelength peeks. Generally, real-time PCR will function if the cycler can emit and detect within ±10 nm to 20 nm of the peak.

| Fluorescing Agent | Excitation/Absorption Peak (nm) | Emission/Detection Peak (nm) |
|---|---|---|
| Fluorescein | 483 to 495 (blue) | 520 to 533 (green) |
| FAM | 483 to 495 (blue) | 520 to 533 (green) |
| SYBR Green I/ Rhodamine green | 480 to 500 (blue) | 520 to 530 (green) |
| Tet | 521 (green) | 536 (green) |
| VIC/HEX/JOE | 523 to 535 (green) | 555 to 568 (green/green-yellow) |
| NED | 546 (green) | 575 (yellow) |
| Cy3 | 550 (green-yellow) | 50 (yellow) |
| TAMRA | 553 (green-yellow) | 576 (yellow) |
| Red 610 | 558 (yellow) | 610 (orange-red) |
| ROX/Texas Red | 585 (yellow-orange) | 605 (orange) |
| Red 640 | 615 (orange-red) | 640 (red) |
| Cy5 | 649 (red) | 670 (red) |
| Cy7 | 743 (red) | 767 (red) |
| Licor IRDyes (several) | 651 to 778 (red-infrared) | 668 to 794 (red-infrared) |

As another embodiment, the bandpass filters could be any combination of single, dual-band, or quad-band bandpass filters with at least 80% transmission in these ranges: 415 nm to 450 nm for excitation of Atto 425, Alexa Fluor 430, and similar fluorescing agents with a corresponding detection bandpass filter with at least 80% transmission in the 470 nm to 510 nm range for the appropriate detection of those fluorescing agents; 460 nm to 495 nm for excitation of FAM, SYBR Green I, and similar fluorescing agents with a corresponding detection bandpass filter with at least 80% transmission in the 515 nm to 548 nm range for the appropriate detection of those fluorescing agents; 480 nm to 505 nm for excitation of SYBR Green I, Rhodamine green Oregon Green 514, and similar fluorescing agents with a corresponding detection bandpass filter with at least 80% transmission in the 525 nm to 565 nm range for the appropriate detection of those fluorescing agents: 505 nm to 533 nm for excitation of JOE, VIC, HEX, and similar fluorescing agents with a corresponding detection bandpass filter with at least 80% transmission in the 553 nm to 600 nm range for the appropriate detection of those fluorescing agents; 530 nm to 555 nm for excitation of NED, TAMRA, Cy3, Rhodamine Red, and similar fluorescing agents with a corresponding detection bandpass filter with at least 80% transmission in the 575 nm to 620 nm range for the appropriate detection of those fluorescing agents; 568 nm to 589 nm for excitation of ROX, Texas Red, Red and similar fluorescing agents with a corresponding detection bandpass filter with at least 80% transmission in the 609 nm to 660 nm range for the appropriate detection of those fluorescing agents; 605 nm to 645 nm for excitation of Cy5 and similar fluorescing agents with a corresponding detection bandpass filter with at least 80% transmission in the 665 nm to 705 nm range for the appropriate detection of those fluorescing agents; and 650 nm to 680 nm for excitation of Cy5.5, Quasar 705, and similar fluorescing agents with a corresponding detection bandpass filter with at least 80% transmission in the 700 nm to 780 nm range for the appropriate detection of those fluorescing agents.

Such detection filter may be sized to be within a predetermined size (e.g., covering an area that is only a portion of the total area of the photodiode detector device that defines the detector). For example, a detector device may include an array of a predetermined number of pixels or individual photodiodes adapted for detection. However, the filter may be sized for allowing transmission of light to only a fraction of the pixels (e.g., less than about 75%, less than about 50%, less than about 25%, less than about 10% or even less than about 5%) available for detection.

Another consideration that may prove beneficial in the performance and operation of the systems herein is the location, angular disposition, and/or spacing of any filter relative to any light source, the sample (and/or holder), the detector, or any combination thereof. For example, suppose that a filter includes generally planar opposing surfaces, though substantial perpendicularity may be possible. There may be an angular disposition of the filter that is less than or greater than perpendicular by at least about 5, 10, 20, 30, 45° or more relative to the principal emission axis from the light source.

One or more filters employed herein may be such that they transmit at least a portion of the emitted visible light (e.g., at least about 50%, 65%, 75% or even 90%), as measured using a suitable spectrometer for optical metrology transmission measurement. One or more filters may be selected to absorb all or substantially all visible light.

It may be desirable for such filters, or one or more other noise reduction filters used in combination therewith to be selected so that wavelengths that translate as background noise are reduced as compared with a system that omits any such filter. By way of example, it is one object to substantially reduce or even eliminate any significant contribution to background noise that may result from infrared radiation arising from any light source used. Desirably, one or more filters may be employed to substantially block infrared radiation (e.g., to block transmission of infrared radiation to a level that is less than about 50%, 60%, 70%, 80%, or even 90% of the total infrared radiation that seeks to be transmitted). Thus, one possible approach may be to employ a filter that transmits at least about 70%, 80% or 90% visible light, but absorbs or otherwise blocks infrared radiation to a level that is less than about 30%, 20% or even 10%.

Among the various filter types that may be employed herein are those such as hot mirrors, heat absorbing glass, shortpass filters, longpass filters, infrared cutoff filters, and wide bandwidth bandpass filters.

Figure 14:
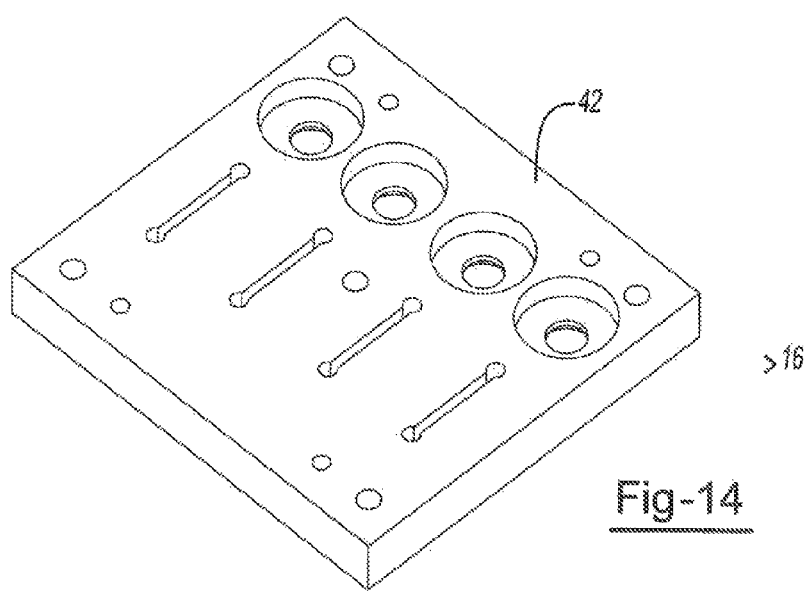
FIG. 14 is a perspective view of an illustrative filter alignment holder in accordance with the present teachings.

Filters herein may have a first face, a generally opposing (e.g., generally parallel) second face, and a periphery that typically spans between the first and second face. It is possible that one or more of any of the filters herein may be at least partially encapsulated (e.g., about at least a portion of its periphery) by a material that differs from the filter. One or more of any of the filters may include a suitable filter alignment holder. Such holder may be adapted to attach to one or more of the other components of the system. For instance, the holder may be sized and configured to receive one or more filters, and may also include an attachment portion (e.g., as part of and/or adjoining a peripheral portion of the holder) that includes suitable structure for attaching the holder within the system. For example, the holder may be such that it can be positioned between a light source and a sample holder, between a sample holder and a detector, or both. A depiction of one example of a filter alignment holder is shown in FIG. 14. The material of the filter alignment holder may be suitable for withstanding the temperature fluctuations to which it may be subjected during operation, such as for avoiding thermal distortion to it, any filter it holds, or both. One approach is to employ a material that has a generally anti-reflective outer surface for avoiding stray emissions. For example, the outer surface to which any light may be directed may be black. Other components within the system (e.g., the one or more boards upon which the circuits are printed) may also be coated or selected to be relatively light absorptive (e.g., they may be generally opaque, such as a black material).

The filter alignment holder may be coupled with the light source. For example, the light source may be supported upon, and/or integrated with one or more circuit boards. One or more filter alignment holder may be coupled with such one or more of such circuit boards. Such coupling may be a permanent coupling that would effectively require destruction of one of the components for detachment. Such coupling may be temporary or removable. For example, one approach may be to employ one or more of an adhesive, a fastener (e.g., a mechanical fastener such as a push pin fastener, a threaded nut assembly, a pin, a clamp or otherwise), a weld (e.g., a stake weld) or any combination of the above. For example, one approach may be to employ a gasket, a layer of adhesive that has a certain amount of compliance and will withstand compression and thermal cycling without distortion, or both. Any filter alignment holder, or combination of filter holders may also have a thickness dimension that is selected to adjust the angle of excitation light that enters the fiber optics and the amount of emission light that reaches the detectors. An example of a suitable material for a filter alignment holder includes thermoplastic or thermoset polymeric containing materials. They may be filled and/or reinforced (e.g., with glass fibers) to help foster dimensional stability during cycling. The filter alignment holder may be made of a material with high thermal mass such that it helps maintain the temperature of the LEDs and detectors at a constant temperature. It may also be desirable to help isolate any metallic materials of the holders from any adjoining circuit boards to help reduce the possibility of electrical interference or short circuits. The filter alignment holder may be assembled in a manner that it includes respective filters for performing the respective functions of filtering light transmitted to a sample, and filtering light emitted by the sample. The filter alignment holder may also include one or more other filter portions that fitter background light.

One approach is to employ a filter alignment holder that includes a different thickness for a transmission portion that transmits light to the sample as compared with the thickness of the holder sample emission portion through which light is emitted to the detector. The transmission portion, for instance desirably will be thick enough to allow light to enter at a relatively small angle of incidence from the light source (e.g., below the angle of incidence of a bandpass filter, which is about 5°). The holder sample emission portion desirably will be relatively thin (e.g. less than about 90%, 75% or even 20% of the thickness of the sample emission portion). The width of the incident area of light emitted from an emission optical fiber is a function of the distance between the terminal end of the fiber and the detector. Since the detector elements are fixed in size (such as about 55 µm by 65 µm), the further the terminal end of optical fiber is located from the detector, the less light that will reach the detector. The optimal thickness of the holder sample emission portion is thus determined by the width of the emission optical fiber bundle and the width of the detector elements. The optimal thickness is also limited by the thickness of the detection filter (such as a linear variable filter or a set of bandpass filters) which may be 1 mm, 2 mm, or even 3 mm thick. One preferred design may have the detection filter directly deposited onto the terminal ends of the optical fibers and thus the filter thickness is negligible. Alternatively, the light source circuitry and the light detection circuitry could be placed on separate circuit boards and the relevant transmission and emission filter holder sections could be optically isolated from each other as a single unit or as separate filter alignment holder components. In this manner, it is believed possible to help reduce the amount of light from the light source that reaches any detector without first exciting the sample to achieve sample emission.

The instrument may include lenses that are present within the optical componentry. More specifically, a lens may be present between the various optical components to improve the efficiency of the excitation and emission means. A lens or lens assembly may be present between the light emitting diode and the excitation bandpass filter, such that the spreading light is converged into substantially parallel beams passing through the filter. An additional converging lens (e.g. biconvex) may be present between the excitation fitter and the waveguide to focus these resulting beams into the waveguide. Such lenses allow for more efficient use of the LED light and homogenize the light entering into the fiber optic waveguide for improved sample excitation. Further, a similar lens arrangement may be employed on the detector side. Light exiting the emission fork portion that is becoming diffuse due to angular incidence may be focused and optimally directed through a detection bandpass filter by a converging lens present there-between. Another converging lens may be present between the detection bandpass filter and photodiode to further focus the light passing through the detection bandpass filter onto the photodiode so that a high efficiency of signal detection is achieved. A lens may also be present between the sample tube and the terminal end of the waveguide proximate thereto. A lens may be integrated into any of the other components, such as attached to the bandpass filter. The instrument may be void of a lens between any of the optical components.

It may also be desirable in the invention to include means for addressing background noise phenomena. A certain level of background noise is commensurate with detector reading and leads to a baseline signal offset which may typically be subtracted during data processing. Due to the temperature dependency and other factors associated with the optical components, signal noise and baseline drift may be experienced during the execution of a real-time protocol. In this sense, it is advantageous to include means for accounting for baseline noise and drift. The use of a reference dye is one such aspect for normalizing signal reads at each cycle. Notwithstanding, it is also contemplated that a separate detector or simply some pixels of each photo-diode array serve as a reference from which any baseline drift may be further corrected.

The teachings herein include componentry enabling for high-speed real time polymerase chain reaction in a mobile, relatively compact instrument. The instrument includes one or more components adapted for transmitting light emitted from a light source (e.g., a light emitting diode device) to one or more samples located in a sample holder. The instrument includes one or more components adapted for transmitting light emitted from at least one fluorescing agent to one or more detectors. A filter (e.g., a linear variable filter) may filter any light emitted by fluorescing material within the one or more samples prior to reaching the detector. A filter (e.g. quad band-pass filter) may filter the light emitted from the light source prior to reaching the sample.

Figure 1A:
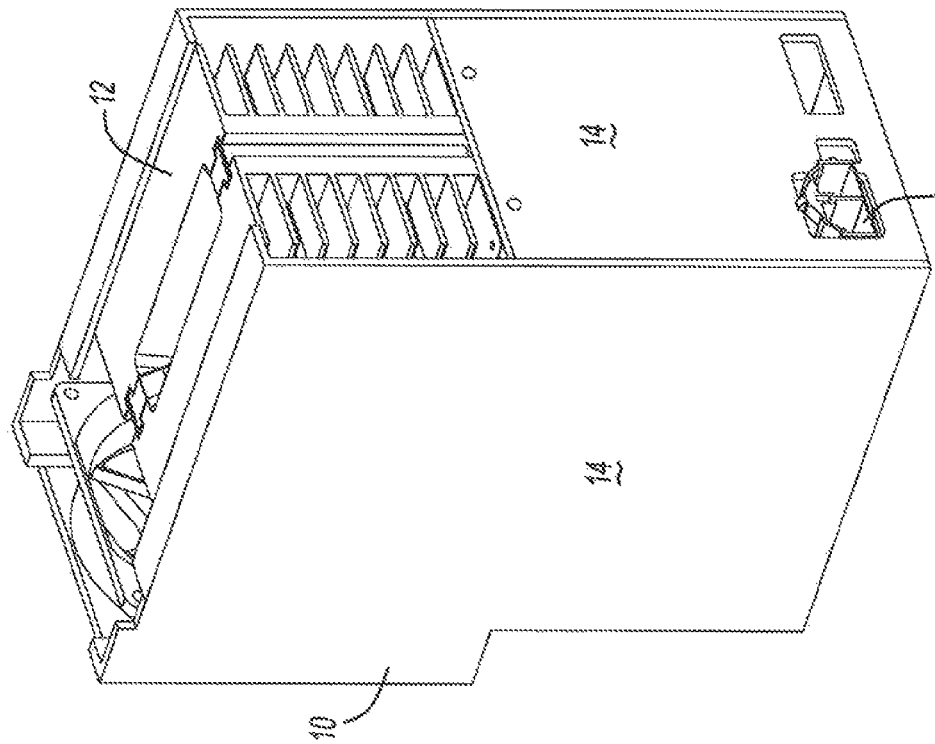
FIG. 1A is a perspective view of an illustrative real-time cycling module in accordance with the present teachings.

As shown for example in FIGS. 1A and 1B, the instrument may include an instrument component portion 10 for housing components including fiber optic and electric componentry 16. The fiber optic and electric components may be located within the instrument below the thermal cycling assembly 12. As shown in FIG. 1A, one or more panels (which may form a sheath) 14 may be included for enclosing the components and for keeping proper airflow to maintain proper component temperature. FIG. 1B shows the components within the instrument with the panels 14 enclosing the components made transparent to expose the fiber optic waveguide and electric componentry 16. One or more electrical components are mounted to a printed circuit board 18.

Figure 2:
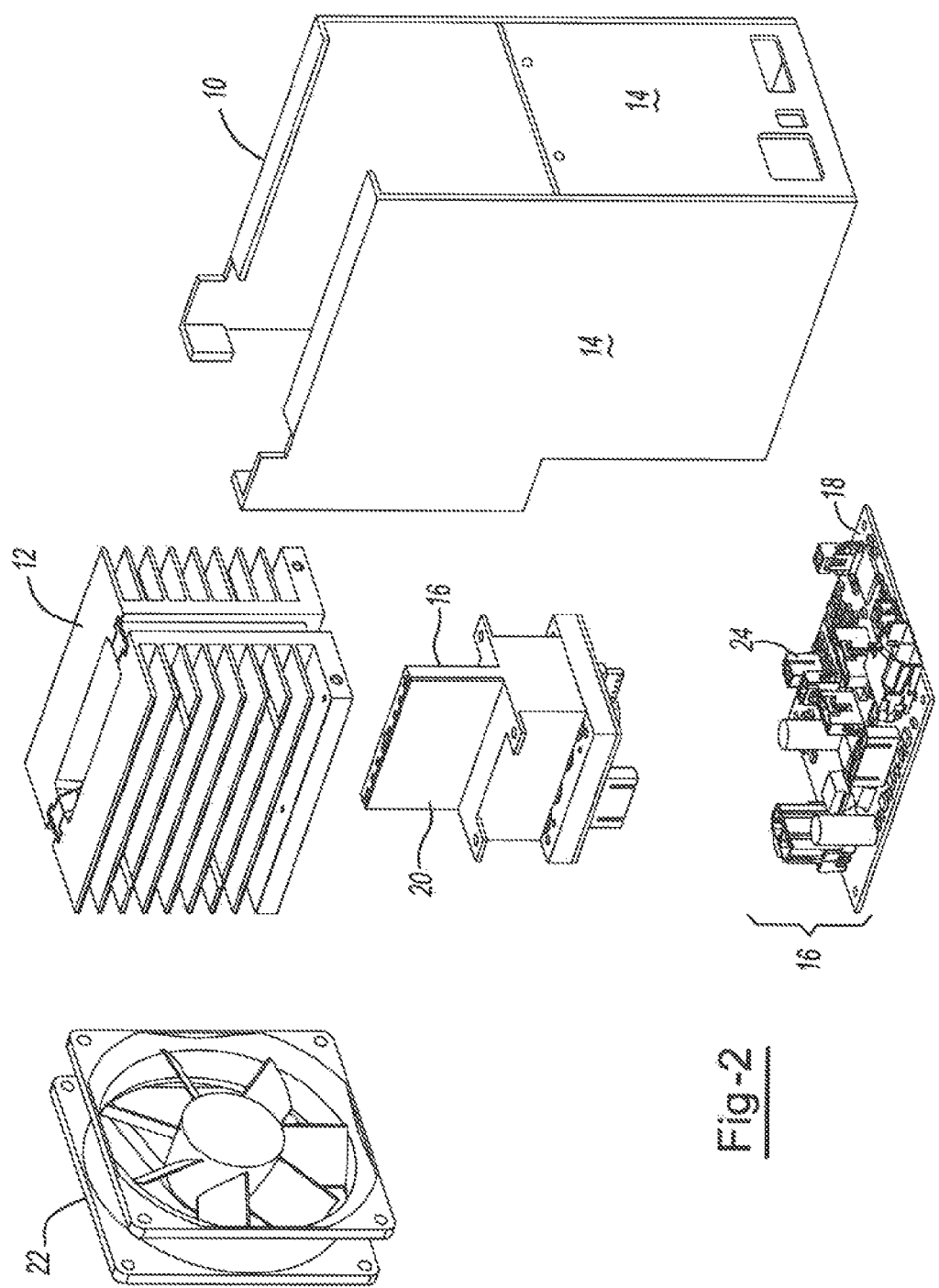
FIG. 2 is an exploded view of the module shown at FIG. 1.

FIG. 2 shows an exploded view of the instrument component portion 10. A plurality of panels 14 is shown for enclosing components therein. The thermocycling assembly 12 is shown above a fiber optics module 20, which is shown above the electronics 24, which together comprise the fiber optic and electrical components 16. The electronics are shown mounted to a platform 18, which may include a printed circuit board (PCB). A fan 22 that is generally located at the back of the instrument component portion 10 is also shown.

Figure 3:
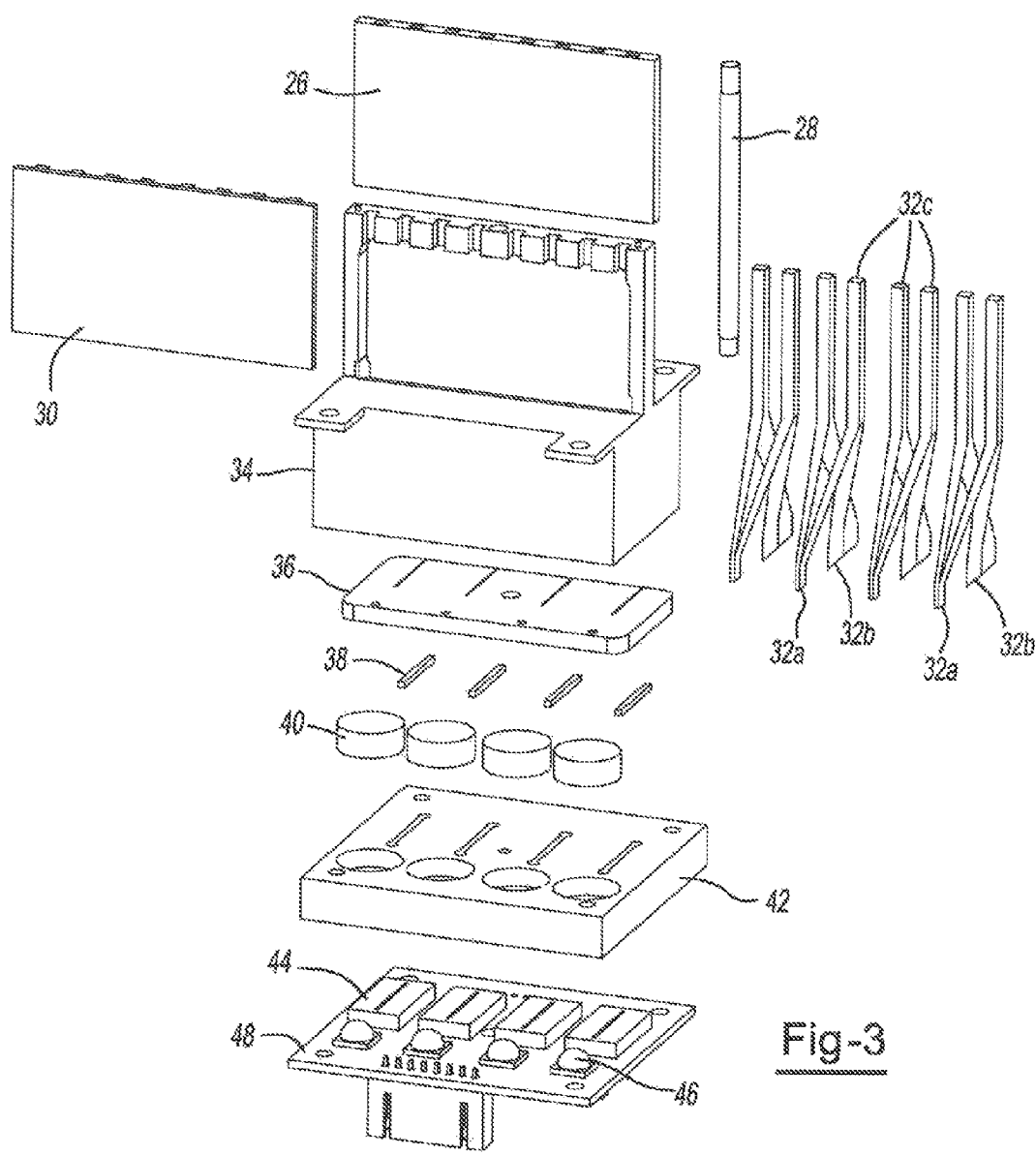
FIG. 3 is an exploded view of an illustrative optical detection module in accordance with the present teachings.

FIG. 3 shows an exploded view illustration of the internal fiber optic and electrical components of the fiber optics module 20. A sample holder 26 is shown for locating within the thermocycling assembly 12 (not shown). A resistance temperature detector (RTD) guide 28 is also shown which travels through a fiber optics block 34 (see FIG. 15 for an additional view of the fiber optics block). A fiber optic cap 30 may be located over and/or onto the fiber optic block 34. A waveguide including one or more fiber optics 32 are located within the fiber optics block 34. The fiber optics 32 may be formed as bifurcated fiber optics, such that a first fork 32a locates over a light source, and a second fork 32b locates over a detector. The first and second fork converge with one another to form a joined arm 32c which is rotated about 90° from the direction of the first and second arm and extends upward toward one or more samples. A bottom cover 36 is located in contact with a bottom edge of the fiber optic block 34. One or more detection filters 38 may be located below the bottom cover and aligned with one or more photodiode arrays 44. One or more light source bandpass filters 40 may be located below the bottom cover and aligned with one or more light sources 46. The one or more detection filters 38 and one or more light source bandpass filters 40 may be located onto a filter alignment holder 42 (see FIG. 14 for an additional view of the filter alignment holder). The filter alignment holder 42 may be located in contact with an optics PCB 48, which may include one or more detectors 44 that correspond to the one or more detection filters 38 and one or more light sources 46 that correspond to one or more light source bandpass filters 40.

Figure 6:
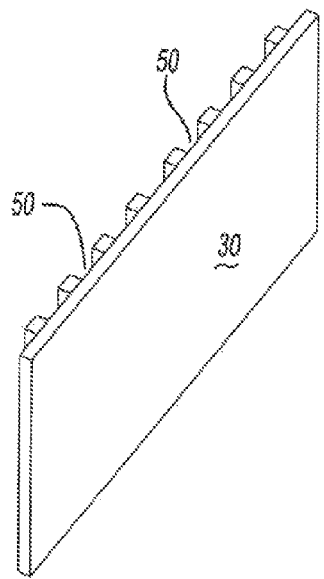
FIG. 6 is a perspective view of an illustrative fiber optics cap in accordance with the present teachings.
Figure 7:
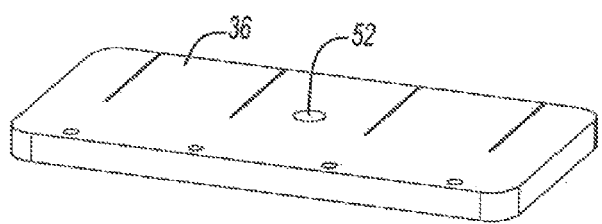
FIG. 7 is a perspective view of an illustrative bottom alignment cover in accordance with the present teachings.

FIGS. 4A and 4B depict an example fiber optics block 34, shown from a top-down view of the fiber optics block. FIG. 4A shows the fiber optics block prior to locating the fiber optics cap onto the block, while FIG. 4B shows the fiber optics cap 30 located onto the block. The fiber optics block is shown including a plurality of recesses 50 for receiving the fiber optics 32 (not shown) and then receiving the fiber optics cap 30 (as shown in detail at FIG. 6). FIGS. 5A and 5B show the fiber optics block 34 as viewed from beneath the block. The RTD guide 28 is shown extending into the bottom of the block. FIG. 5A shows the block prior to addition of the bottom cover, whereas the bottom cover 36 is shown located onto the block in FIG. 5B. The bottom cover 36 (as shown in detail in FIG. 7) may include an opening 52 for receiving and/or being substantially aligned with the RTD guide (as shown in detail in FIG. 10).

Figure 8:
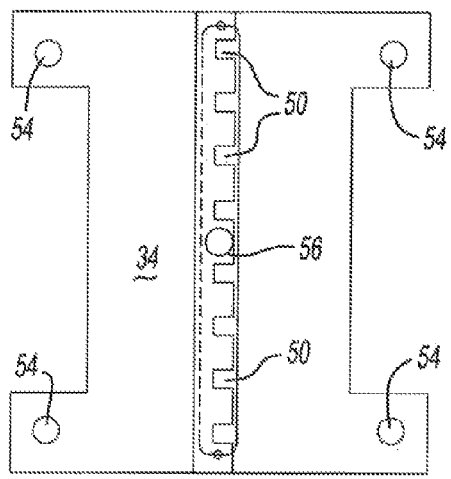
FIG. 8 is a top-down view of the fiber optics block of FIG. 4A.
Figure 9:
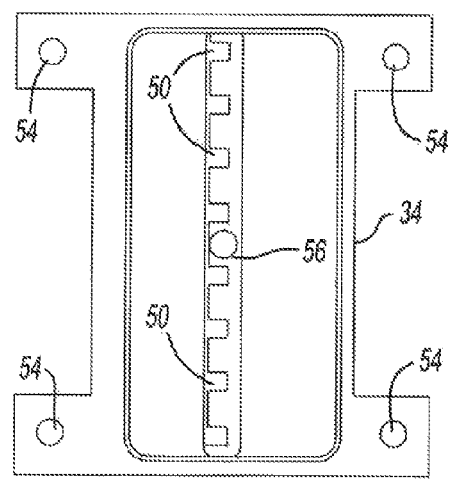
FIG. 9 is a bottom-up view of the fiber optics block of FIG. 4A.

FIG. 8 shows an additional top-down view of an example fiber optics block 34, while FIG. 9 shows an additional bottom-up view of the fiber optics block. The views include the plurality of recesses 50 for aligning with and receiving the fiber optics cap 30. The resulting gap formed between the block 34 and the cap 30 forms an opening for the fiber optics 32 to align directly under each sample in the sample holder 26. One or more gaps may be formed between the block 34 and the cap 30. Each gap is an opening for the fiber optics 32 to align directly under each sample in the sample holder 26. An opening 56 may be formed in the block for receiving the RTD guide. The opening 56 may be located in a substantially centralized location along the block 34. The block may further include a plurality of openings 54 adapted for attaching the block to a surface within the instrument. The block 34 may be potted with a resin or similar material to permanently keep the assembled block together, to protect the fiber optics 32, and to keep the fiber optics stationary.

Figure 10:
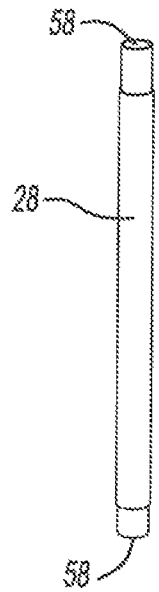
FIG. 10 is perspective view of an illustrative RTD guide.

The RTD guide 28 is shown in further detail at FIG. 10. The RTD guide preferably includes one or more tapered ends 58 for entering into one or more openings within the fiber optics block. The RTD guide is hollow to allow an RTD (not shown) to pass through the block 34 and measure the temperature of the sample holder 26.

Figure 11:
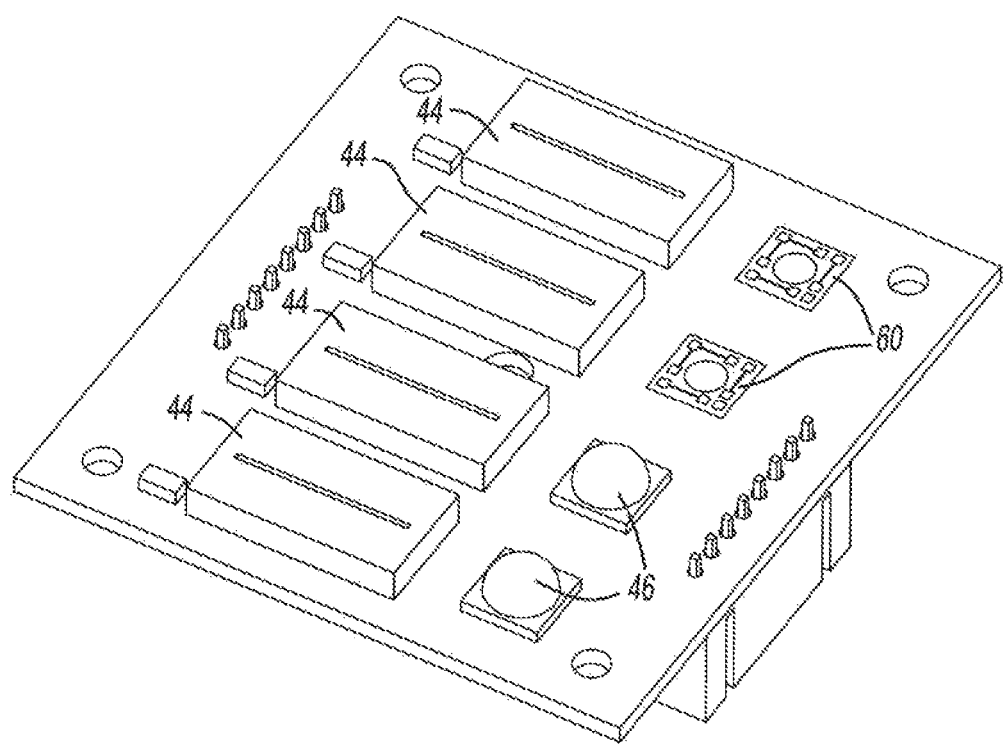
FIG. 11 is a top-down view of an illustrative circuit board in accordance with the present teachings.

As discussed with reference to FIG. 3, a printed circuit board (PCB) 48 is included within the instrument, an example of which is shown at FIG. 11. The PCB includes one or more detectors 44, the number of detectors times the number of sample regions per detector corresponding with the number of PCR samples per module. For example, the four detectors 44 shown each have two sample regions per detector corresponding to eight samples. The PCB further includes one or more light sources 46. In the illustrative embodiment, each light source 46 contains four different wavelength LEDs. For illustrative purposes, the PCB is shown having two surfaces 60 to which light sources have not been attached.

In the illustrative figures, each light emitting diode device provides light to two samples and each detector has two sample regions (i.e. one for each sample). Other numerical strategies are contemplated. For example, each light emitting diode device may provide light to even more samples, such as four or even eight samples. On the other hand, each sample could have its own light emitting diode device. In this instance it would be possible for a detector with only one sample region to be shared by multiple samples by sequential timing of the light emitting diode devices. Given the short read times required for each sample, a sequential sample read strategy may have insignificant impact on total read time. In the extreme, each sample may have dedicated light sources and detectors. However, communal strategies would reduce the total number of components required and thus the required space and overall cost of the instrument.

In one embodiment, for each sample there is one light emitting diode device and one photodiode detector device. In another embodiment, for every two samples there is exactly one light emitting diode device and two photodiode detector devices. Alternatively, for every two samples there are exactly two light emitting diode devices and one photodiode detector device. In yet another embodiment, for every four samples there is one light emitting diode device and four photodiode detector devices. Alternatively, for every four samples there are four light emitting diode devices and one photodiode detector device. In yet another embodiment, for every eight samples there is one light emitting diode device and eight photodiode detector devices. Alternatively, for every eight samples there are eight light emitting diode devices and one photodiode detector device. In the instances where an unbalanced number of light emitting diode devices and photodiode detector devices are employed, the optical reading process may be executed in such a way that the signal from each sample can be isolated. By way of illustration, for a shared photodiode detector device the light emitting diode devices are energized at different times (sample 1 measured, then sample 2, etc.). In a preferred embodiment, there are individual photodiode detector devices for each sample with shared light emitting diode devices such that multiple samples may be read simultaneously.

Another embodiment of the invention may include a step of locating the light emitting diode device above the sample holder. Excitation of the sample may be provided through transmission of light through the cap and may include the multiple band pass filter and additional fiber optic cables to transmit the light to the sample. In this instance, the light transmission assembly below the sample holder would be comprised of waveguides for transmission of light emitted by the fluorescing agent to the detector.

Figure 12:
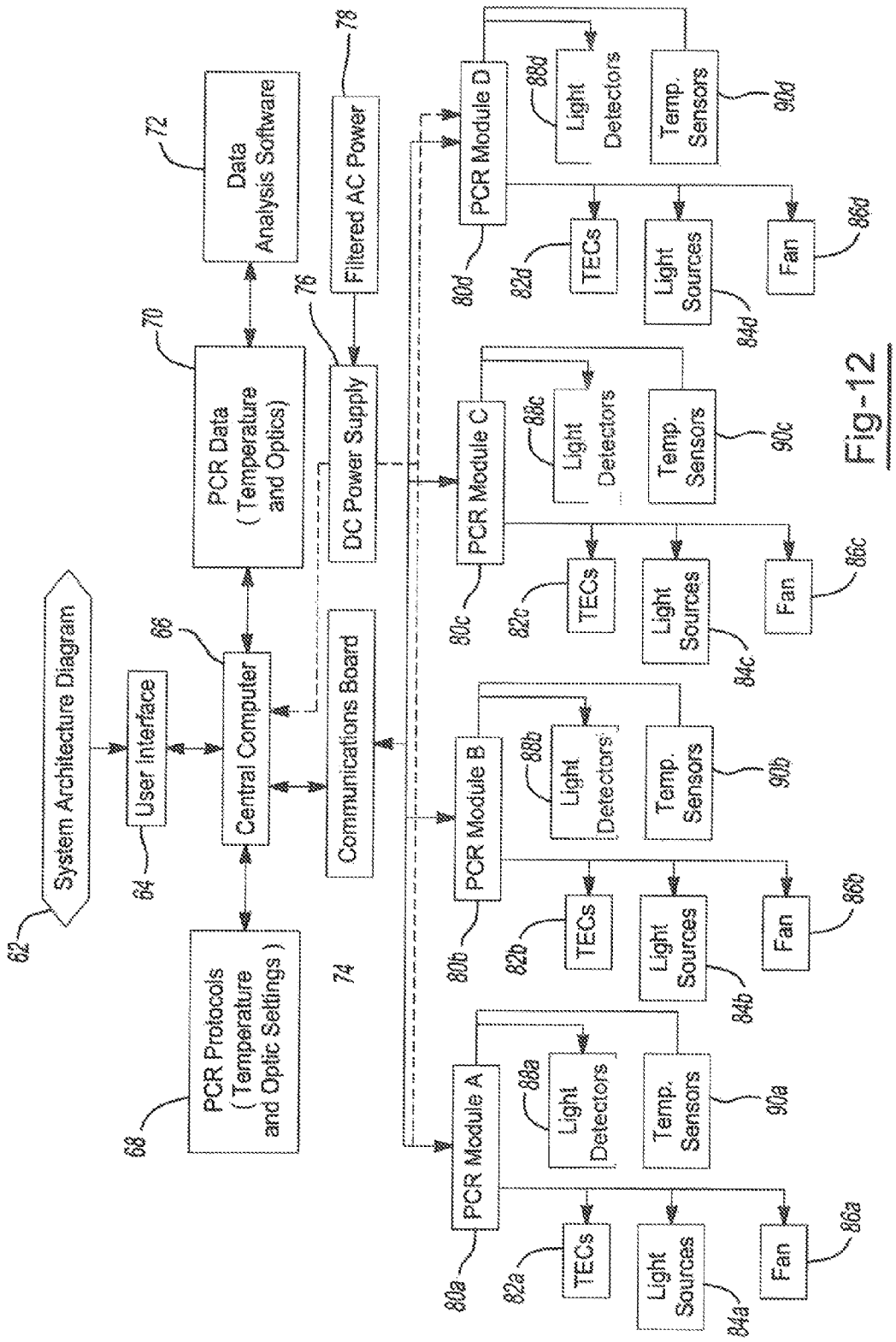
FIG. 12 is a flow diagram showing an illustrative relationship among the components of an instrument in accordance with the present teachings.

A flow-chart depicting connectivity of the instrument described herein with an illustrative four thermocycling modules is shown at FIG. 12. The system architecture diagram shows the central computer 62 as controlling the user interface 64, PCR protocols 68 (including temperature and optics settings), PCR data 70 (including temperature and optics data), and the communications board 74. The PCR data 70 is also in communication with data analysis software 72 which provide for usable data storage and statistical analysis resulting from the PCR protocols. The central computer 66 further optionally receives power from a DC power supply 76 if the computer is internal to the instrument, otherwise the computer has its own DC power supply. DC power supply 76 receives power from a filtered AC power source 78. The communications board 74 is in direct two-way communication with each PCR module (depicted in this example as 80a, 80b, 80c and 80d). Each PCR module also receives power from the DC power supply 76. Each PCR module provides communications to a thermoelectric cooler (TEC) device 82a, 82b, 82c, 82d; a light source 84a, 84b, 84c, 84d; and a fan device 86a, 86b, 86c, 86d. Each PCR module receives communication from one or more temperature sensors 90a, 90b, 90c, 90d. Each PCR module is in two-way communication with one or more light detectors 88a, 88b, 88c, 88d.

Each module may be mostly self-contained. Each module may be independently controllable and may perform real-time PCR on up to 2, up to 8, up to 12, or even up to 20 samples. The module includes all necessary electronics and optics (controller board, H-bridge, sensors, thermal protection, LEDs, optical detection hardware, etc) with the exception of the power supply and user interface. Each module may be contained in a sheath (e.g., plurality of panels) 14 for optimum airflow to keep the samples uniform in temperature. The airflow may also go past all sensitive electronics, detectors, and light sources, keeping them cool. The sheath 14 may also serve as a protective barrier separating the hot components, electrified circuits, and static sensitive components from the user and external elements. The module may have one 2-wire connector for power, and one 2-wire connector for communication with the user-interface electronics. Alternatively the module may have one 4-wire connector which handles both power and communication. This minimal wiring keeps the modules easy to install, maintain, replace, calibrate, and allows for the modules to be easily placed within an instrument box or as external add-ons to existing equipment. The wiring connections 94 may extend out the side of the module as shown in FIG. 1A, or may extend out of the bottom of the module. The wiring connections may be plugs and receptacles or pins and matching pin terminals for easy module installation and removal. The modules may be fully independent, individually calibrated, may be swapped for easy repair/maintenance, may be produced in an instrument with 1, 2, 3, 4, or more modules, and are generally small and portable. The modules may be pre-programmed so that no user interface software or computer is required (ideal for medical applications and ease of use). The modules may be programmed by a barcode scanner, 2D barcode scanner, NFC (near field communications), or RFID (radio frequency identification) from an appropriate test kit, assay, or sample tube.

Figure 13:
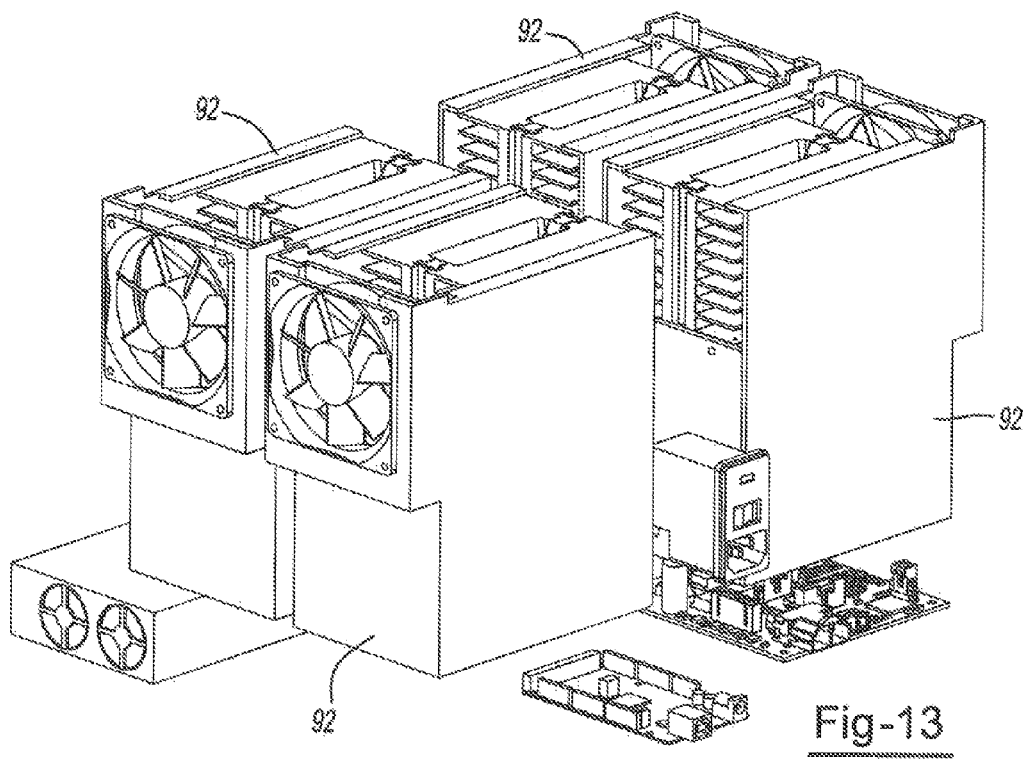
FIG. 13 is a perspective view of an illustrative 4-module instrument in accordance with the present teachings.
Figure 15:
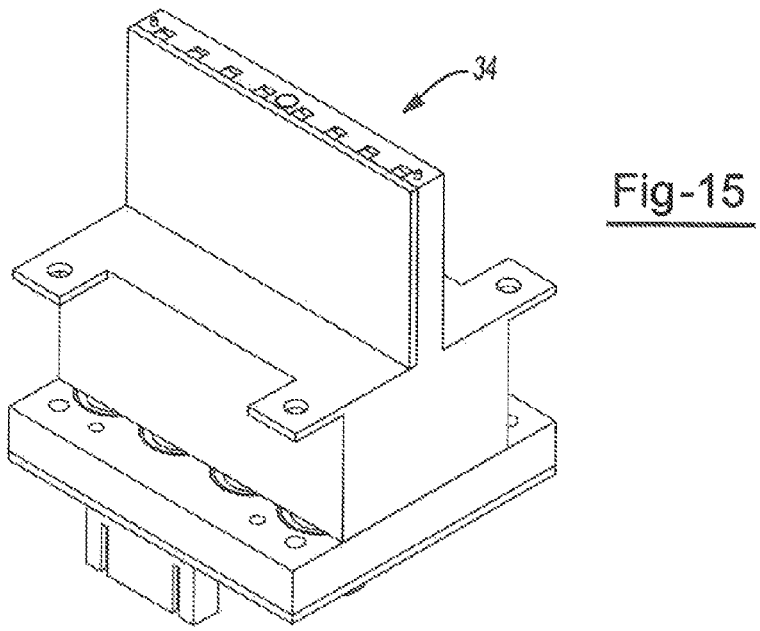
FIG. 15 is a perspective view of an illustrative fiber optic block in accordance with the present teachings.
Figure 16:
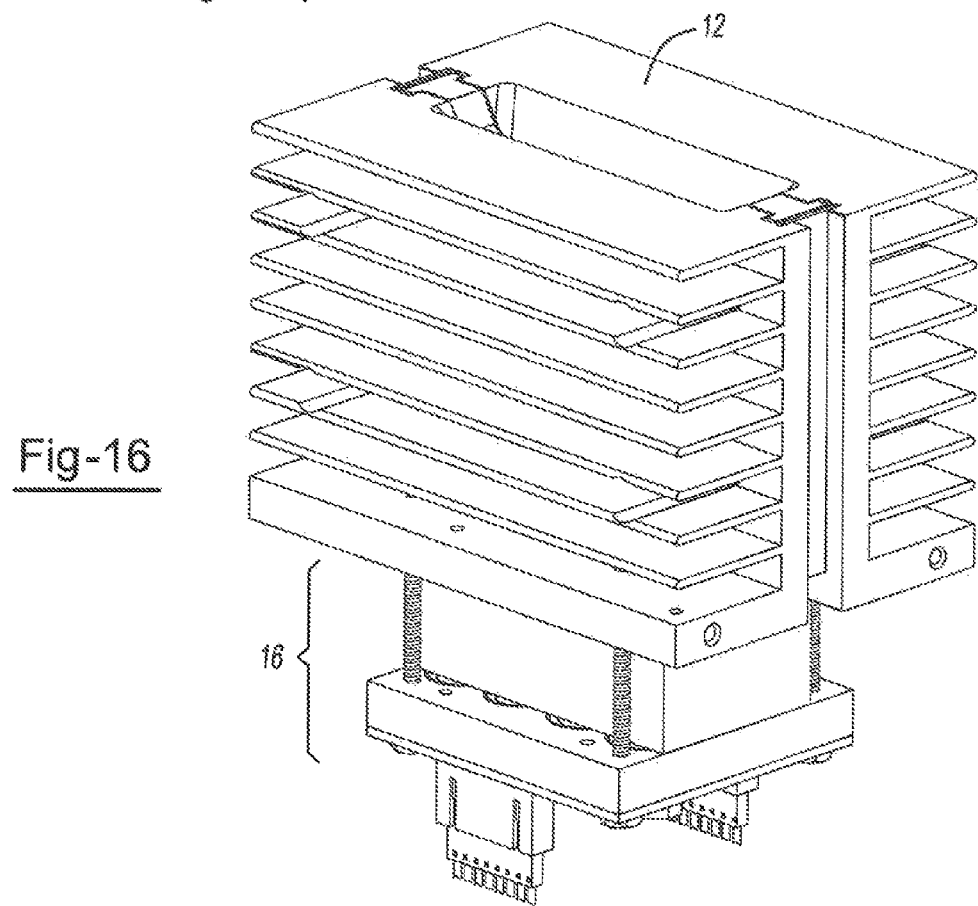
FIG. 16 is a perspective view of an illustrative sample block/fiber optic block module in accordance with the present teachings.

FIG. 13 shows an example instrument including four separate PCR modules 92, each module including a sample holder and each sample holder having its own fiber optic componentry. FIG. 14 shows an exemplary filter alignment holder 42 showing additional detail for shape and arrangement of openings within the filter holder for receiving filter components. FIG. 15 shows an additional perspective of the fiber optics block 34. FIG. 16 shows a sample block 12 and connected fiber optic and electrical components 16 below.

FIG. 18 shows a side view of an embodiment of the first excitation fork portion. A light emitting diode device 110 shines light through a LED lens array 108. The LED lens array 108 focuses the light emitted from the individual elements of the light emitting diode device 110 through bandpass filters located in the excitation filter holder 106. The filtered light continues to the excitation fiber lens 104 which focuses all of the filtered light beams to the fiber optic bundle 102. The fiber optic bundle 102 contains at least one optical fiber 100 in a compact staggered arrangement to minimize the amount of light lost to unusable space between the optical fibers 100. The optical fiber 100 transmits the filtered light to at least one sample tube (not shown) and may be flexible or bent into a permanent configuration to allow for precise alignment with the sample tube. The light emitting diode device 110 may be an integrated assembly of light emitting diodes or the light emitting diode device 110 may be a compact group of individual light emitting diodes located on a substrate such as a printed circuit board, with an arrangement such that the light emitting diodes require an area which is less than 3 cm per side, or less than 1 cm per side, or even less than about 4 mm per side. The group of light emitting diode elements may have at least one color, at least 4 colors, at least 5 colors, or at least 7 colors. The light emitting diode elements may be repeated such that more than one element has the same color in the light emitting diode device 110 to increase intensity of that color and/or to increase the overall life-span of using that color. The LED lens array 108 could be a single integrated component as shown in FIG. 18, or a compact arrangement of individual lenses. The lens arrangement in the LED lens array 108 would match the pattern of light emitting diodes in the light emitting diode device.

In one embodiment shown in FIG. 18, the lenses are staggered in the LED lens array 108. In another embodiment the LED lens array is in a rectangular grid arrangement (as example of which is available from Edmund Optics, Barrington, N.J. under the designation #64-486). The excitation filter holder 106 may be a stationary device that holds individual bandpass filters. There may be one bandpass filter for each LED element in the light emitting diode device 110 as shown in FIG. 19. In another embodiment, one or more multi-band bandpass filter may filter light from more than one LED element in the light emitting diode device 110. The excitation filter holder 106 may be a moving filter wheel that holds bandpass or multi-band bandpass filters as shown in FIG. 20. The excitation fiber lens 104 may be a single converging lens designed to transmit light from all of the LED elements to the fiber optic bundle 102. In another embodiment the excitation fiber lens may be an array of individual lenses. The optical fibers 100 may be designed with a relatively large numerical aperture (0.55 or greater) to maximize the light that is transmitted to the samples. The optical fibers 100 may be plastic or they may be glass such as borosilicate selected to have high light transmission in the about 400 nm to about 700 nm range. The optical fibers 100 may have a diameter of about 0.1 mm, 0.25 mm, 0.5 mm, or even 1.0 mm. The optical fibers 100 may all go to a single sample tube or the optical fibers may be split to go to more than one sample tube. The optical fibers may go to the top of the sample tube so that the light can be transmitted through the optically clear cap of the sample tube. The optical fibers may go to the bottom of the sample tube so that the light can be transmitted through the optically clear bottom portion of the sample tube. The grouping of the light emitting diode device 110, LED lens array 108, excitation filter holder 106, excitation fiber lens 104, and optionally one end of the fiber optic bundle 102 may be enclosed in a filter alignment holder (not shown). The filter alignment holder blocks light from entering or escaping the first excitation fork portion other than through the optic fibers 100; holds the excitation fiber lens 104, filter holder 106, and LED lens array 108 in proper alignment with the light emitting diode device 110 and the fiber optic bundle 102; and can withstand and potentially dissipate heat generated from the light emitting diode device 110.

FIG. 19 shows a perspective view of one preferred embodiment of the first excitation fork portion. There are seven light emitting diodes located in a staggered arrangement on the light emitting diode device 110. Each light emitting diode element is approximately 1 mm×1 mm such that the entire hexagonal grouping of light emitting diode elements occupies a space of less than about 4 mm×4 mm. The LED lens array 108 is a single optically clear array which is staggered such that each lens is approximately centered over the top of the individual light emitting diode elements of the light emitting diode device 110. The excitation filter holder 106 contains seven bandpass filters with an optical density of less than 1, less than 0.1, or even less than 0.01 in the desired wavelength ranges and an optical density of greater than 4, greater than 5, or even greater than 6 in the undesired wavelength ranges. There are up to seven different bandpass filters to match the up to seven different light emitting diode elements. A single excitation fiber lens 104 focuses the seven filtered light paths to a grouping of 32 staggered optical fibers 100 of 0.33 mm diameter and a 0.55 numerical aperture which are tightly grouped in the fiber optic bundle 102. The grouping of 32 staggered optical fibers may be split to transmit light through 32 optical fibers to one sample, 16 optical fibers each to two samples, eight optical fibers each to four samples, or four optical fibers each to eight samples. Another embodiment may use 16 optical fibers with each sample receiving light from 16, 8, 4, or 2 optical fibers respectively depending on the number of samples. Another embodiment may use 64 optical fibers with each sample receiving light from 64, 32, 16, or 8 optical fibers respectively.

FIG. 20 shows a side view and perspective view of another preferred embodiment of the first excitation fork portion. There are seven light emitting diodes located in a staggered arrangement on the light emitting diode device 110. Each light emitting diode element is approximately 1 mm×1 mm such that the entire hexagonal grouping of light emitting diode elements occupies a space of less than 4 mm×4 mm. The LED lens array 108 is a single optically clear array which is staggered such that each lens is approximately centered over the top of the individual light emitting diode elements of the light emitting diode device 110. The excitation filter holder 106 is comprised of an excitation filter wheel 112 which contains approximately seven bandpass filters 116 with an optical density of less than 1, less than 0.1, or even less than 0.01 in the desired wavelength ranges and an optical density of greater than 4, greater than 5, or even greater than 6 in the undesired wavelength ranges and a motor 114 which turns the filter wheel. There are seven different bandpass filters 116 to match the different light emitting diode elements. A single excitation fiber lens 104 focuses the seven filtered light paths to a grouping of optical fibers 100 in the fiber optic bundle 102. In another embodiment, there may be fewer than seven bandpass filters if one or more of the light emitting diode element is repeated to emit approximately the same color in the light emitting diode device 110. In another embodiment, there may be more than seven bandpass filters if it is desirable to use more than one waveband from one or more of the light emitting diode elements to fine-tune the filtered light.

Figure 21:
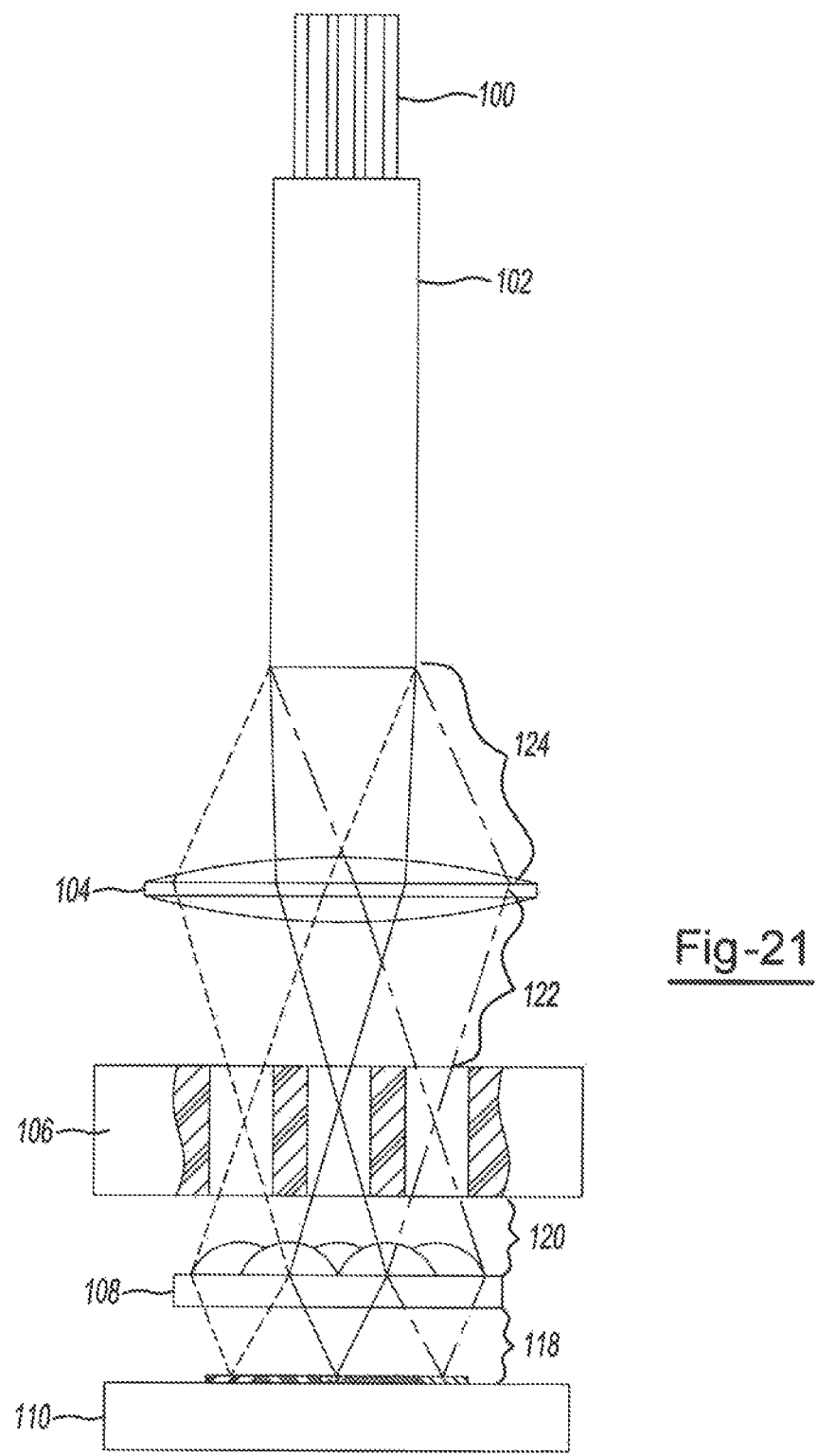
FIG. 21 is a side profile view of an illustrative light path of the fork portion of FIG. 18.

FIG. 21 is a representative drawing of the light path through the embodiment of FIG. 18 and FIG. 19. Light from the light emitting diode 110 spreads away from the light emitting diode element and through the LED to lens space 118. The LED to lens space 118 is small (less than 3 mm, less than 2 mm, or even less than 1 mm) such that the bulk of the light from a single light emitting diode element goes to a single desired lens in the LED lens array 108. Light focused through the LED lens array 108 passes through the lens array to excitation filter holder space 120. Light may focus in a crossing pattern through the excitation filter holder 106 as shown in FIG. 21 or the light may be approximately collinear and perpendicular to the light emitting diode device 110. The filtered light passes through the excitation filter to excitation fiber lens space 122 and then is focused by the excitation fiber lens 104 to pass through the excitation fiber lens to fiber optic bundle space 124. The distances of the spaces 118, 120, 122, and 124 are chosen to maximize the amount of light that reaches the optical fibers 100 at a light angle that the optical fibers can accept depending on the numerical aperture of the optical fibers and the specific lens designs. The total distance from the light emitting diode device 110 to the fiber optic bundle 102 may be less than 1 cm, less than 5 cm, or even less than 10 cm.

Figure 22:
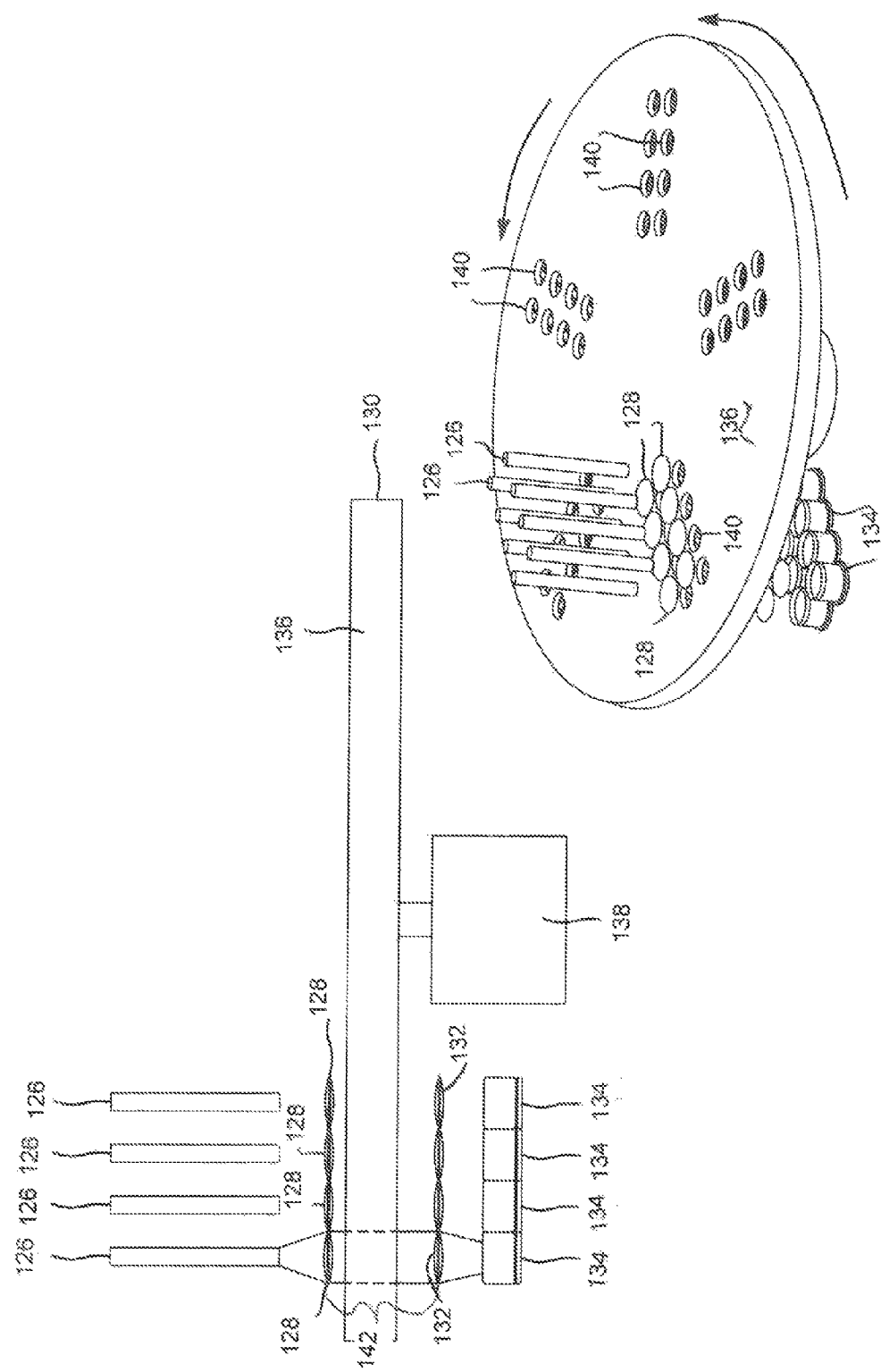
FIG. 22 is an exploded side profile and perspective view of an illustrative fork portion in accordance with the present teachings.

FIG. 22 shows an embodiment of the second detection fork portion. Detection optical fibers 126 collect light from the sample tubes and transmit that light to the detection fiber to filter lens 128. In FIG. 22, one representative light path 142 is shown. The detection fiber to filter lens 128 could be an array of individual lenses or an integrated lens array. The detection fiber to filter lens 128 focuses the light from the detection optical fibers 126 into an approximately collinear path that is approximately perpendicular to the detection filter holder 130 and the photodiode detector device 134. Detection filter holder 130 is comprised of a motor 138 that rotates the filter wheel 136 and various detection bandpass filters 140. Light is filtered by the detection bandpass filters 140, is focused by filter to detector lens 132, and is detected by photodiode detector device 134. The components are arranged in FIG. 22 such that each detection fiber 126 has one detection to filter lens 128, one detection bandpass filter 140, one filter to detector lens 132, and one photodiode detector 134. However, many other configurations also may be utilized. More than one detection fiber 126 could share an optical path through the lenses, filters, and to the detector. A bandpass filter 140 could be large enough to be shared by multiple light paths to reduce the number of components required. The detection fiber to filter lens 128 and/or fitter to detector lens 132 could be individual lenses or an integrated array of lenses. The photodiode detector device 134 could be an integrated device with an array of photodiode elements or an array of separate photodiode detectors. The bandpass filters 140 could be a single wavelength band or could be multi-band bandpass filters to minimize the number of components and reduce the number of filter wheel rotations that are necessary. The number of bandpass or multi-band bandpass filters 140 determines the number of colors that could be detected which may allow for 1, 2, 3, 4, 5, 6, 7, 8, 9, 10, or more different colors to be detected. The bandpass filters could be arranged such that all photodiode detectors in the photodiode detector device 134 receive the same light wavelength simultaneously, or they could be arranged such that each photodiode in the photodiode detector device receives different wavelengths of light.

One or both of the detection fiber to filter lens 128 and/or filter to detector lens 132 could be removed if the detection area of the photodiode detection device 134 is large enough to accept most or all of the light spread from the detection optical fibers 126. Minimizing the distance between the detection optical fibers 126 and the photodiode detection device 134 will assist in minimizing that light spread. For example a distance of 10 mm, 5 mm, or 3 mm or less is desirable. In FIG. 22 the components (fiber optics, lenses, bandpass filters, and photodiode detectors) are arranged in two rows of four. However, many other configurations exist. The shape of the grouping could be one single row of eight, a curved row, or other grouping such as a round or square arrangement. Multiple detection fibers 126 could share the same lenses, filters, and photodiode to increase the light sensitivity. The detection filter wheel 136 could be distinct and separate from the excitation filter wheel 112 or they could be the same filter wheel which shares the same motor 114/138. This combination of filter wheels 112 and 136 minimizes the number of components and ensures simultaneous timing of the excitation and detection filters. The entire second detection fork portion is enclosed in a detection filter alignment holder (not shown). The detection filter alignment holder blocks light from the surroundings, especially any light that may escape from the first excitation fork portion. All or part of detection filter alignment holder may act as a thermal insulator such that the photodiode detection device 134 will not be impacted by higher temperatures generated in the instrument. All of part of the detection filter alignment holder may act as a thermal conductor to remove heat generated by the photodiode detection device 134.

Figure 23:
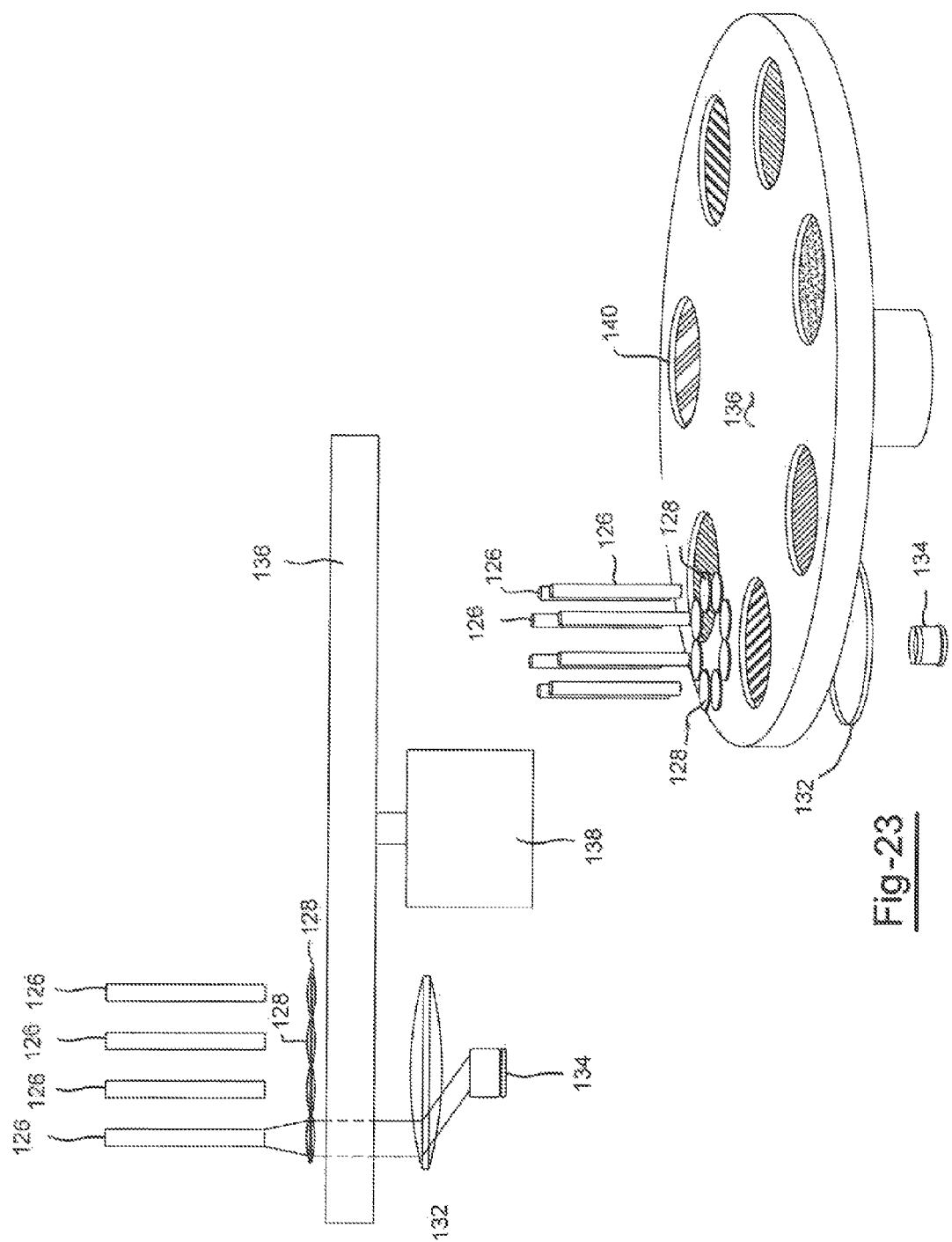
FIG. 23 is an exploded side profile and perspective view of an illustrative fork portion in accordance with the present teachings.

FIG. 23 shows another embodiment of the second detection fork portion. In this case the filter to detector lens 132 is large enough to be shared by all light paths from all detection fibers 126. The large filter to detector lens 132 focuses light onto a single photodiode detection device 134. This arrangement allows for a reduction in the number of components and assurance that the photodiode detection device sensitivity is the same for all light paths. The large filter to detector lens 132 could be a single converging filter as shown in FIG. 23 or a lens array of individual lenses which focuses each detection light path onto the same photodiode detection device 134.

Figure 24:
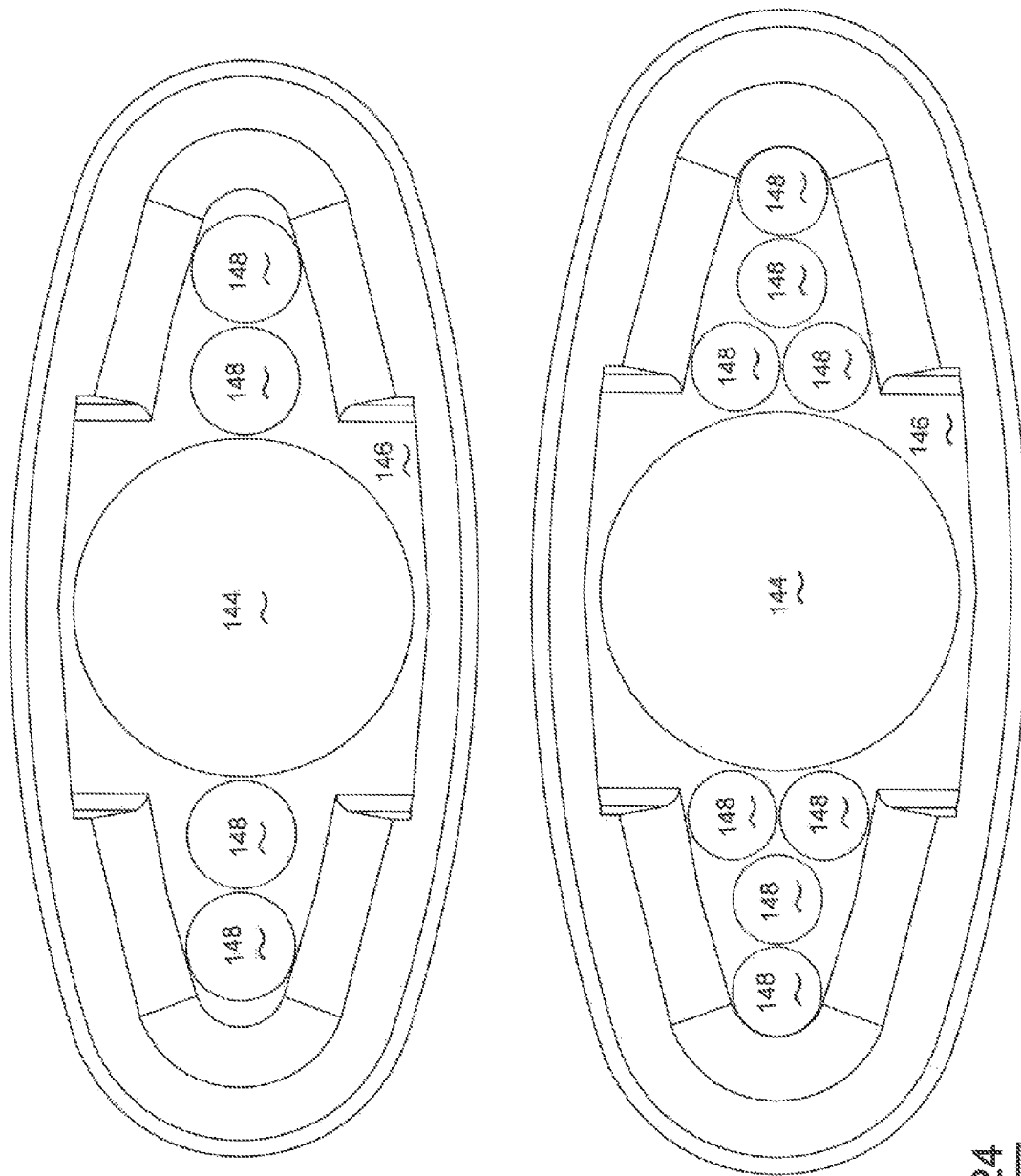
FIG. 24 is a bottom view of an illustrative sample tube and optical fibers in accordance with the present teachings.

FIG. 24 shows the bottom of a sample tube. This sample tube has optically clear bottom portion which has a low optical density of less than 1, less than 0.1, or even less than 0.01 to light in the about 450 nm to about 750 nm wavelength range. The tube bottom 150 is comprised of a flat tube portion 146 and an angled/curved tube portion 148. The light can transfer to/from the sample within the tube and to/from optical fibers underneath the tube through the flat tube portion 146 with minimal light reflection, light distortion, and light absorption due to the flat, thin, and parallel inner/outer surfaces of the sample tube bottom. Optical fibers 142 carry excitation light from the first excitation fork portion of the optical manifold 100, within fiber optic bundle 102, and transmit that light into the sample tube. Two potential configurations of the optical fibers 142 are shown in FIG. 24. In the top image of FIG. 24, there are four excitation optical fibers 142, two on either side of the flat tube portion 146; in the bottom image of FIG. 24 there are eight excitation optical fibers 142, four on either side of the flat tube portion 146. The optical fibers are shown to be of maximal diameter in each configuration to fit within the flat tube portion 146 in order to maximize the amount of light that is transferred per excitation optical fiber. The excitation optical fibers 142 have a diameter of about 0.33 mm and about 0.25 mm respectively in FIG. 24. There may be other configurations in which there are additional, but smaller, excitation optical fibers 142 to increase the surface area which is covered by the excitation optical fibers 142 and therefore increase amount of light that can be transferred. The optical fibers may also extend into the angled/curved tube portion 148; however, there is diminished light transmission in those regions. A large diameter emission optical fiber 144 is centered underneath the flat tube portion 146. The large diameter and placement of the emission optical fiber 144 allows for maximum surface area and therefore maximum amount of fluorophore emission light to be passed through a single fiber. The diameter may be about 0.5 mm, about 0.75 mm, about 1.0 mm, or even about 1.25 mm. In another configuration, there may be more than one emission optical fiber 144 with diameters which are smaller in order to remain within or mostly within the flat tube portion 146. For example, there may be four emission optical fibers 144 which are about 0.5 mm in diameter and placed within the center of the flat tube portion 146. The emission optical fiber 144 may be round as shown in FIG. 24 or it may be a molded optically transparent plastic with a more rectangular shape which acts as a light pipe. The emission optical fiber may be optically transparent to light with an optical density of less than 1, less than 0.1, or even less than 0.01 in the about 450 nm to about 750 nm wavelength range.

As to all of the foregoing general teachings, as used herein, unless otherwise stated, the teachings envision that any member of a genus (list) may be excluded from the genus; and/or any member of a Markush grouping may be excluded from the grouping.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Invention of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints. Concentrations of ingredients identified in Tables herein may vary ±10%, or even 20% or more and remain within the teachings.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. An instrument for performing polymerase chain reaction with real-time detection comprising:
   (a) a sample holder having one or more sample wells, wherein the one or more sample wells are configured to receive one or more sample tubes which are optically transparent along a bottom portion opposite a cap opening of each of the sample tubes, and that receives a biological sample having a nucleic acid to be amplified and at least one fluorescing agent that interacts with the nucleic acid during amplification and that emits light upon excitation by light of a known wavelength;
   (b) at least one light emitting diode device that is carried on at least one support substrate, is in electrical communication with a power source, is adapted to emit light at a plurality of different wavelengths, and is located below the sample holder so that the sample holder receives light emitted from the at least one light emitting diode device at a bottom of the sample holder;
   (c) at least one photodiode detector device carried on the at least one support substrate and adapted to issue signals based upon intensity of light it receives;
   (d) a light transmission assembly that includes:
      (i) at least one waveguide which at least partially extends into the one or more sample wells of the sample holders and includes a joined arm which extends into bifurcated portion, wherein the bifurcated portion includes:
         1) at least one first excitation fork portion that extends between the sample holder and the at least one light emitting diode device for transmitting light emitted from the at least one light emitting diode device to the biological sample contained in the sample holder to excite the at least one fluorescing agent; and
         2) at least one second emission fork portion that extends between the sample holder and the at least one photodiode detector device for transmitting light emitted by the at least one fluorescing agent upon its excitation and having a first end that is proximate the sample holder and a second end that is proximate the at least one photodiode detector device; and
      (ii) a housing located between the sample holder and the at least one support substrate, which receives the at least one waveguide, and includes:
         1) an upper portion aligned with the sample holder;
         2) a base portion having a cavity therein through which the bifurcated portion is passed; and
         3) a bottom cover having one or more ports which are aligned with the at least one light emitting diode device;
   (e) a linear variable band pass filter, series of bandpass filters, or a multiple band bandpass filter disposed between the second end of the at least one second emission fork portion and the at least one photodiode detector device and is adapted to filter the light emitted by the at least one fluorescing agent across a plurality of bandwidths so that the wavelengths of light received by the at least one photodiode detector device are known; and
   (f) opposing thermoelectric devices which sandwich the sample holder and the upper portion of the housing.

2. The instrument of claim 1, wherein the at least one light emitting diode device is an integrated assembly of LEDs or a compact group of light emitting diodes; and
   wherein the at least one light emitting diode device is less than 1 cm on each side.

3. The instrument of claim 1, wherein the at least one photodiode detector device is a photodiode pixel array or compact grouping of photodiodes, such that the wavelengths of light received across individual pixels or photodiodes are of known wavelengths corresponding to different fluorescent agent(s) present within the one or more sample tubes.

4. The instrument of claim 1, wherein the light transmission assembly is located below the sample holder.

5. The instrument of claim 1, wherein for each sample there is one of the at least one light emitting diode device and one of the at least one photodiode detector device.

6. The instrument of claim 1, wherein the instrument includes a plurality of sample holders, each of which can be subjected to independent protocols simultaneously.

7. The instrument of claim 1, wherein for every two samples there is exactly one of the at least one light emitting diode device and two of the at least one photodiode detector devices.

8. The instrument of claim 1, wherein for every two samples there is exactly one of the at least one photodiode detector device and two of the at least one light emitting diode devices.

9. The instrument of claim 1, wherein each of the at least one light emitting diode device includes at least 4 light emitting diode elements.

10. The instrument of claim 1, at least one converging lens is present between the second end of the at least one second emission fork portion and the at least one photodiode detector device.

11. The instrument of claim 1, wherein the at least one photodiode detector device is arranged as an array elongated thin strips of pixels.

12. The instrument of claim 1, wherein the bottom portion of the one or more sample tubes is comprised of a flat tube portion having two substantially parallel planar surfaces; and
    wherein the two substantially parallel planar surfaces are an inner surface and an outer surface of the flat tube portion.

13. The instrument of claim 1, wherein the linear variable band pass filter or the series of bandpass filters are optically aligned with a plurality of pixels of the at least one photodiode detector device.

14. The instrument of claim 1, wherein a multiple wavelength band pass filter is disposed between the at least one first excitation fork portion and the at least one light emitting diode device and is adapted to filter the light emitted by the at least one light emitting diode device into multiple bandwidths for excitation of the biological sample; and
    wherein the multiple wavelength band pass filter is a quad band bandpass filter.

15. The instrument of claim 14, wherein at least one converging lens is present between the at least one light emitting diode device and an end of the at least one first excitation fork portion.

16. The instrument of claim 3, wherein some of the individual pixels of each of the at least one photodiode detector device or a separate detection means are employed as a reference to compensate for baseline phenomena such as baseline offset and drift of sample measurements.

17. The instrument of claim 1, which includes at least one detection fiber, at least one detection to filter lens, at least one detection bandpass filter, at least one filter to detector lens; and
    wherein the at least one detection fiber collects light from the one or more sample tubes and transmits the light to the at least one detection to filter lens, the light is filtered by the at least one detection bandpass filter, and the light is detected by the at least one photodiode detector device.

18. The instrument of claim 1, wherein the instrument includes a multiple wavelength band pass filter disposed between the at least one first excitation fork portion and the at least one light emitting diode device and is adapted to filter the light emitted by the at least one light emitting diode device into multiple bandwidths for excitation of the biological sample.

19. The instrument of claim 1, wherein the instrument is part of a fiber optics module which is located within a thermal cycling assembly.

20. An instrument for performing polymerase chain reaction with real-time detection comprising:
    (a) a sample holder having one or more sample wells, wherein the one or more sample wells are configured to receive one or more sample tubes that each have at least one bottom portion opposite a cap opening that is generally optically transparent, and that receives a biological sample having a nucleic acid to be amplified and at least one fluorescing agent that interacts with the nucleic acid during amplification and that emits light upon excitation by light of a known wavelength;
    (b) at least one light emitting diode device with a lens, wherein the at least one light emitting diode device is carried on at least one support substrate, is in electrical communication with a power source, is located below the sample holder so that the sample holder receives light emitted from the at least one light emitting diode device at a bottom of the sample holder, and includes at least four light emitting diodes each adapted to emit light at a different wavelength relative to each other;
    (c) at least one heat sink carried on the at least one support substrate for dissipating heat from the at least one light emitting diode device;
    (d) at least one photodiode detector device carried on the at least one support substrate and adapted to issue signals that are proportionally based upon intensity of light it receives and including a photodiode array which comprises a plurality of discrete pixels or photodiodes;
    (e) a light transmission assembly that is positioned below the sample holder and that includes:
        1) at least one waveguide which at least partially extends into the one or more sample wells of the sample holders and includes a joined arm extending to a bifurcated portion, wherein the bifurcated portion includes:
            (i) a first fork portion that extends between the sample holder and the at least one light emitting diode device for transmitting light emitted from the at least one light emitting device to the biological sample contained in the sample holder to excite the at least one fluorescing agent; and
            (ii) a second fork portion that extends between the sample holder and the photodiode array for transmitting light emitted by the at least one fluorescing agent upon its excitation and having a first end that is proximate the sample holder and a second end that is proximate the at least one photodiode detector device;
        2) a housing located between the sample holder and at the at least one support substrate, which receives the at least one waveguide, and includes:
            (i) an upper portion aligned with the sample holder;
            (ii) a base portion having a cavity through which the first fork portion and the second fork portion of the at least one waveguide extend through; and
            (iii) a bottom cover portion for the cavity of the housing that includes one or more ports is aligned with the lens of the at least one light emitting diode devices and an opening for aligning the second end of the second fork portion with the at least one photodiode detector device;

(f) a linear variable band pass filter or discrete series of bandpass filters that is disposed between the second end of the second fork portion and the at least one photodiode detector device, wherein the linear variable band pass filter or the discrete series of bandpass filters is generally optically aligned with predetermined discrete pixels of the photodiode array, so that the wavelengths of light received by the discrete pixels of the photodiode array are known upon detection of light by the photodiode array; and (g) a multiple wavelength band pass filter disposed between the first fork portion and the at least one light emitting diode device and is adapted to simultaneously filter the light emitted by the at least one light emitting diode device into multiple bandwidths for excitation of the biological sample; and (h) opposing thermoelectric devices which sandwich the sample holder and the upper portion of the housing.

* * * * *

UNITED STATES PATENT AND TRADEMARK OFFICE
CERTIFICATE OF CORRECTION

PATENT NO. : 9,932,632 B2  Page 1 of 1
APPLICATION NO. : 13/833349
DATED : April 3, 2018
INVENTOR(S) : Kreifels et al.

It is certified that error appears in the above-identified patent and that said Letters Patent is hereby corrected as shown below:

In the Claims

Column 34, Line 18, Claim 1 delete "which extends into bifurcated" and insert --which extends into a bifurcated--

Column 34, Line 44, Claim 1 delete "pass filter, series" and insert --pass filter, a series--

Signed and Sealed this
Fifth Day of June, 2018

Andrei Iancu
*Director of the United States Patent and Trademark Office*